United States Patent
Capobianco et al.

(10) Patent No.: US 12,275,725 B2
(45) Date of Patent: Apr. 15, 2025

(54) INHIBITORS OF THE NOTCH TRANSCRIPTIONAL ACTIVATION COMPLEX AND METHODS FOR USE OF THE SAME

(71) Applicants: University of Miami, Miami, FL (US); StemSynergy Therapeutics, Inc., Miami, FL (US)

(72) Inventors: Anthony J. Capobianco, Miami Beach, FL (US); Mark Spyvee, Hampstead, NH (US); Luisana Astudillo, North Miami, FL (US); Darren Orton, Miami, FL (US)

(73) Assignees: University of Miami, Miami, FL (US); StemSynergy Therapeutics, Inc., Miami, FL (US)

( * ) Notice: Subject to any disclaimer, the term of this patent is extended or adjusted under 35 U.S.C. 154(b) by 792 days.

(21) Appl. No.: 17/602,311

(22) PCT Filed: Feb. 11, 2020

(86) PCT No.: PCT/US2020/017685
§ 371 (c)(1),
(2) Date: Oct. 8, 2021

(87) PCT Pub. No.: WO2020/209933
PCT Pub. Date: Oct. 15, 2020

(65) Prior Publication Data
US 2022/0194932 A1    Jun. 23, 2022

Related U.S. Application Data

(60) Provisional application No. 62/832,538, filed on Apr. 11, 2019.

(51) Int. Cl.
*C07D 417/12* (2006.01)
*A61P 35/00* (2006.01)
*C07D 403/12* (2006.01)

(52) U.S. Cl.
CPC ............ *C07D 417/12* (2013.01); *A61P 35/00* (2018.01); *C07D 403/12* (2013.01)

(58) Field of Classification Search
CPC ...... C07D 417/12; C07D 403/12; A61P 35/00
See application file for complete search history.

(56) References Cited

U.S. PATENT DOCUMENTS

| | | | |
|---|---|---|---|
| 7,879,893 B2 | 2/2011 | Olsen et al. | |
| 10,501,413 B2 | 12/2019 | Capobianco et al. | |
| 2012/0251551 A1 | 10/2012 | Lucking et al. | |
| 2014/0329867 A1 | 11/2014 | Radtke et al. | |
| 2018/0086700 A1 | 3/2018 | Capobianco et al. | |
| 2021/0171469 A1 | 6/2021 | Capobianco et al. | |

FOREIGN PATENT DOCUMENTS

| | | |
|---|---|---|
| WO | WO-200949423 A1 | 4/2009 |
| WO | WO-2009/064486 A9 | 7/2009 |
| WO | WO-2014/062811 A2 | 4/2014 |
| WO | WO-2016/154255 A1 | 9/2016 |
| WO | WO-2018/187845 A1 | 10/2018 |
| WO | WO-2018/211090 A1 | 11/2018 |
| WO | WO-2019/001416 A1 | 1/2019 |

OTHER PUBLICATIONS

Extended European Search Report mailed on Dec. 9, 2022, for European Patent Application No. 20787427.2, 8 pages.
Wu, S. et al. (Nov. 2006). "Anticancer activity of 5-benzylidene-2-phenylimino-1, 3-thiazolidin-4-one (BPT) analogs," *Medicinal Chemistry* 2(6):597-605.
Aster et al., Oncogenic forms of Notch1 lacking either the primary binding site for RBP-Jkappa or nuclear localization sequences retain the ability to associate with RBP-Jkappa and activate transcription, J. Biol. Chem., 272(17):11336-11343 (1997).
Astudillo et al., The small molecule IMR-1 inhibits the notch transcriptional activation complex to suppress tumorigenesis, Cancer Research, 76(12):3593-3603 (2016).
Beharry et al., "Novel benzylidene-thiazolidine-2, 4-diones inhibit Pim protein kinase activity and induce cell cycle arrest in leukemia and prostate cancer cells," Mol. Cancer Ther., 8:1473-1483 (2009).
Berezovska et al., Aspartate mutations in presenilin and gamma-secretase inhibitors both impair notch1 proteolysis and nuclear translocation with relative preservation of notch1 signaling, J. Neurochem., 75(2):583-593 (2000).
Espinoza et al., "Notch inhibitors for cancer treatment", Pharmacology & Therapeutics, 139:95-110 (2013).
Extended European Search Report, which includes the supplementary European search report and the European search opinion, for European Patent Application No. 16769567.5, issued Aug. 24, 2018.
Fischer et al., Anti-DLL4 inhibits growth and reduces tumor-initiating cell frequency in colorectal tumors with oncogenic KRAS mutations, Cancer Res., 71(5):1520-1525 (2011).
International Application No. PCT/US20/17685, International Search Report and Written Opinion, mailed May 22, 2020.
International Application No. PCT/US2019/016868, International Preliminary Report on Patentability, mailed Aug. 31, 2020.
International Application No. PCT/US2019/016868, International Search Report and Written Opinion, mailed Jun. 14, 2019.
International Preliminary Report on Patentability, for International Application No. PCT/US2016/023691, issued Sep. 26, 2017.
International Search Report and Written Opinion of the International Searching Authority, for International Application No. PCT/US2016/023691, dated Jun. 21, 2016.
Jeffries et al., Characterization of a high-molecular-weight Notch complex in the nucleus of Notch(ic)-transformed RKE cells and in a human T-cell leukemia cell line, Mol. Cell Biol., 22(11):3927-3941 (2002).

(Continued)

*Primary Examiner* — Jeffrey S Lundgren
*Assistant Examiner* — W. Justin Youngblood
(74) *Attorney, Agent, or Firm* — Mintz, Levin, Cohn, Ferris, Glovsky and Popeo, P.C.

(57) ABSTRACT

Disclosed herein are inhibitors of the Notch transcriptional activation complex, and methods for their use in treating or preventing diseases, such as cancer. The inhibitors described herein can include compounds of Formula (I) and pharmaceutically acceptable salts thereof: Formula (I), wherein the substituents are as described.

20 Claims, 6 Drawing Sheets

(56) References Cited

OTHER PUBLICATIONS

King, Bioisosteres, conformational restriction, and pro-drugs—Case history: An example of a conformational restriction approach, Med Chem: Principle & Practice, p. 206-9 (1994).
Kloe et al., Small molecules that inhibit Notch signaling, Methods Mol. Biol., 1187:311-322 (2014).
Kovall et al., Crystal structure of the nuclear effector of Notch signaling, CSL, bound to DNA, EMBO J., 23(17):3441-3451 (2004).
Kovall, More complicated than it looks: assembly of Notch pathway transcription complexes, Oncogene, 27(38):5099-5109 (2008).
McGuffin et al., IntFold: an integrated server for modelling protein structures and functions from amino acid sequences, Nucleic Acids Res., 43(W1):W169-W173 (2015).
Moellering et al., Direct inhibition of the Notch transcription factor complex, Nature, 462:182-188 (2009).
Nam et al., Structural basis for cooperativity in recruitment of MAML coactivators to Notch transcription complexes, Cell, 124(5):973-983 (2006).
PubChem CID 1305511, Methyl [5-(2-bromo-4-ethoxy-5-methoxybenzylidene)-3-methyl-4-oxo-2-thioxo-1-imidazolidinylacetate, created Jul. 10, 2005.
PubChem-CID-50848794, Create Date: (Feb. 22, 2011).
PubChem-CID-50848832, Create Date: (Feb. 22, 2011).
PubChem-CID-83829010, Create Date: (Oct. 20, 2014).
Ranganathan et al., Notch signalling in solid tumours: a little bit of everything but not all the time, Nat. Rev. Cancer, 11(5):338-351 (2011).
Russell et al., "Selective small molecule inhibitors of the potential breast cancer marker, human arylamine N-acetyltransferase 1, and its murine homologue, mouse arylamine N-acetyltransferase 2", Bioorganic & Medicinal Chemistry, 17:905-918 (2009).
Sharma et al., A monoclonal antibody against human Notch1 ligand-binding domain depletes subpopulation of putative breast cancer stem-like cells, Mol. Cancer Ther., 11(1):77-86 (2012).
Shih et al., Notch signaling, gamma-secretase inhibitors, and cancer therapy, Cancer Res., 67(5):1879-1882 (2007).
Takebe et al., Targeting notch signaling pathway in cancer: clinical development advances and challenges, Pharmacol. Ther., 141(2):140-149 (2014).
Tamura et al., Physical interaction between a novel domain of the receptor Notch and the transcription factor RBP-J kappa/Su(H), Curr. Biol., 5(12):1416-1423 (1995).
Taylor, Protein kinases: a diverse family of related proteins, Bioessays, 7(1):24-29 (1987).
Tiyanont et al., Insights into Notch3 activation and inhibition mediated by antibodies directed against its negative regulatory region, J. Mol. Biol., 425(17):3192-3204 (2013).
Wang et al., Notch signaling drives stemness and tumorigenicity of esophageal adenocarcinoma, Cancer Research, 74(21):6364-6374 (2014).
Weaver et al., Nack is an integral component of the Notch transcriptional activation complex and is critical for development and tumorigenesis, Cancer Research, 74(17):4741-4751 (2014).
Williams et al., Structural basis for the potent and selective binding of LDN-212854 to the BMP receptor kinase ALK2, Bone., 109:251-258 (2018).
Wu et al., "Anticancer Activity of 5-Benzylidene-2-Phenylimino-1,3-Thiazolidin-4-one (BPT) Analogs", Medicinal Chemistry, vol. 2, No. 6, pp. 597-605 (2006).
Yap et al., "Small-Molecule Inhibitors of the ERK Signaling Pathway: Towards Novel Anticancer Therapeutics", ChemMedChem, 6:38 (2011).

Input: nuclear proteins

INHIBITORS OF THE NOTCH TRANSCRIPTIONAL ACTIVATION COMPLEX AND METHODS FOR USE OF THE SAME

STATEMENT OF GOVERNMENT SUPPORT

This invention was made with government support under grant numbers CA083736 and CA125044 awarded by the National Institutes of Health. The government has certain rights in the invention.

BACKGROUND OF THE INVENTION

Field of the Invention

The present disclosure relates to inhibitors of the Notch transcriptional activation complex, and methods of using the inhibitors to decrease Notch target gene transcription and to treat and prevent diseases, such as cancer.

Description of Related Technology

The Notch pathway, a highly conserved cell signaling system present in most multicellular organisms, is widely used in development to govern cell fate specification, and to balance proliferative capacity and differentiation state. Notch drives a context-dependent cellular response by initiating and maintaining a transcriptional cascade. Notch mediates this transcriptional response by directing the formation of a core Notch transcriptional activation complex ("NTC"), which is composed of the DNA binding protein CSL, the intracellular domain of Notch ("NICD") and the co-activator protein Mastermind ("MAML1").

In the adult, the Notch pathway is restricted to small populations of progenitor and stem cells of regenerating tissues, such as the colon and brain. However, in many human cancers, the Notch pathway becomes reactivated. The deregulation of the Notch pathway underlies many aspects of cancer physiology, depending on cell type and context. Aberrant Notch activity has been demonstrated to play a role in the initiation and maintenance of the neoplastic phenotype, as well as playing a central role in cancer stem cells, which may underlie a role in metastasis and resistance to therapy.

Current compounds that regulate the Notch pathway include small molecule inhibitors that target the presenilin-dependent γ-secretase, an enzyme complex that is responsible for ligand-induced cleavage and activation of Notch, monoclonal antibodies that inhibit ligand-receptor interactions, and small molecule inhibitors that directly target the intracellular Notch pathway or the assembly of the transcriptional activation complex.

There is a need for more potent, bioavailable, and metabolically stable antineoplastic therapeutics capable of directly targeting the Notch transcriptional activation complex for the treatment and prevention of diseases, such as cancer.

SUMMARY OF THE INVENTION

In one aspect, the disclosure provides compound of Formula (I), or a pharmaceutically acceptable salt thereof:

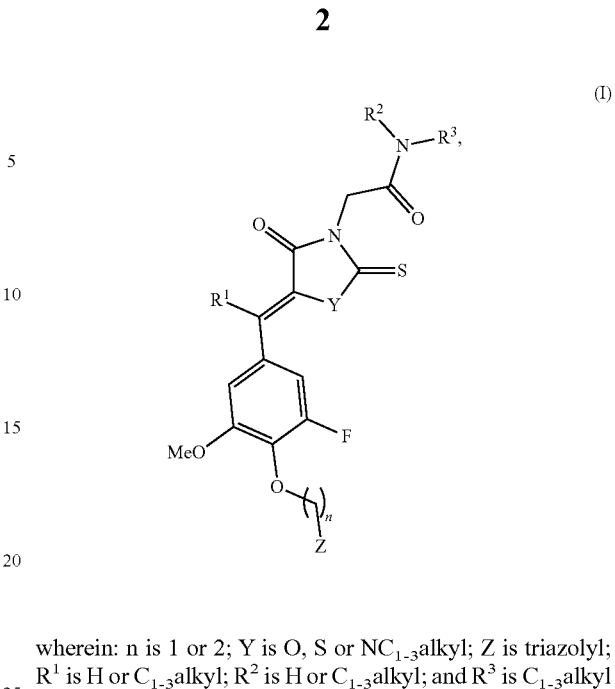

wherein: n is 1 or 2; Y is O, S or $NC_{1-3}$alkyl; Z is triazolyl; $R^1$ is H or $C_{1-3}$alkyl; $R^2$ is H or $C_{1-3}$alkyl; and $R^3$ is $C_{1-3}$alkyl or halophenyl. In some embodiments, n is 1. In various embodiments, n is 2. In some cases, Y is O. In various cases, Y is S. In some embodiments, Y is $NCH_3$. In various embodiments, Z is

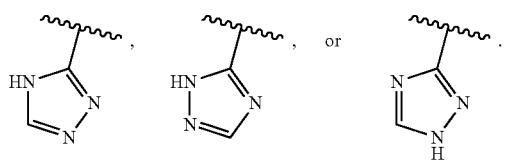 [SMILES: *c1nnc[nH]1 ; *c1ncn[nH]1 ; *c1nc[nH]n1]

In some cases, Z is

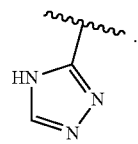

In various cases, $R^1$ is H. In some embodiments, $R^1$ is $CH_3$. In various embodiments, $R^2$ is H. In some cases, $R^2$ is $CH_3$. In various cases, $R^3$ is $CH_3$. In some embodiments, $R^3$ is chlorophenyl. In various embodiments, $R^3$ is para-chlorophenyl. In some cases, $R^2$ is $CH_3$ and $R^3$ is $CH_3$. In various cases, $R^2$ is H and $R^3$ is chlorophenyl. In some embodiments, n is 1; Y is S; $R^1$ is $CH_3$; $R^2$ is $CH_3$; and $R^3$ is $CH_3$. Contemplated compounds of the disclosure include a compound is selected from the group consisting of:

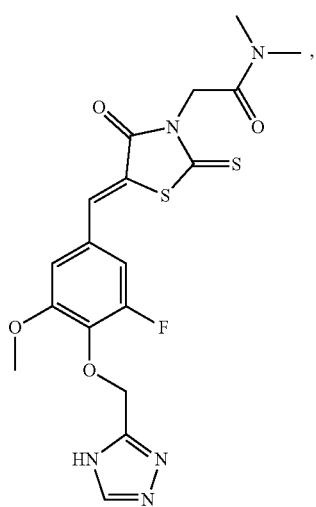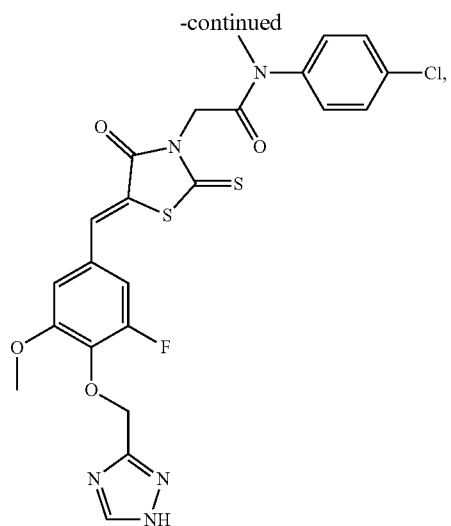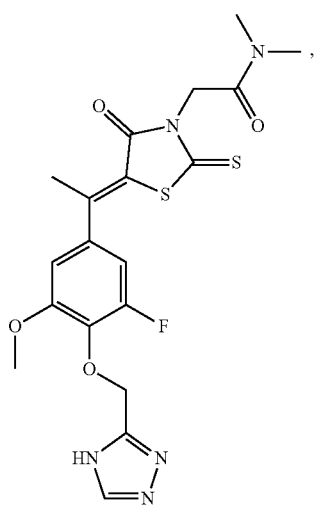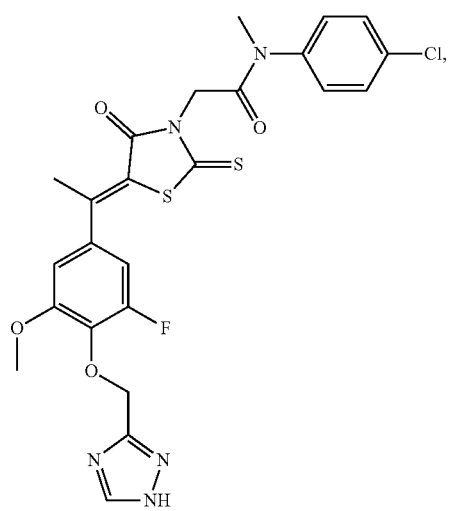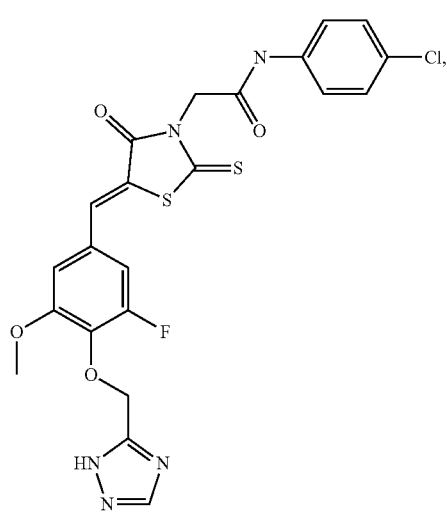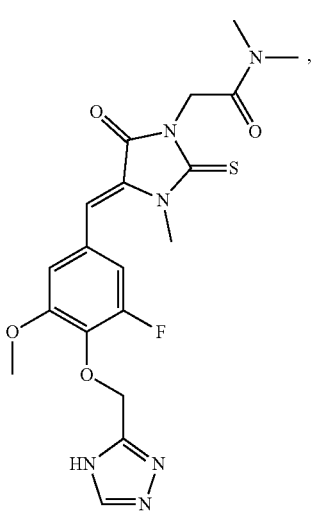

-continued

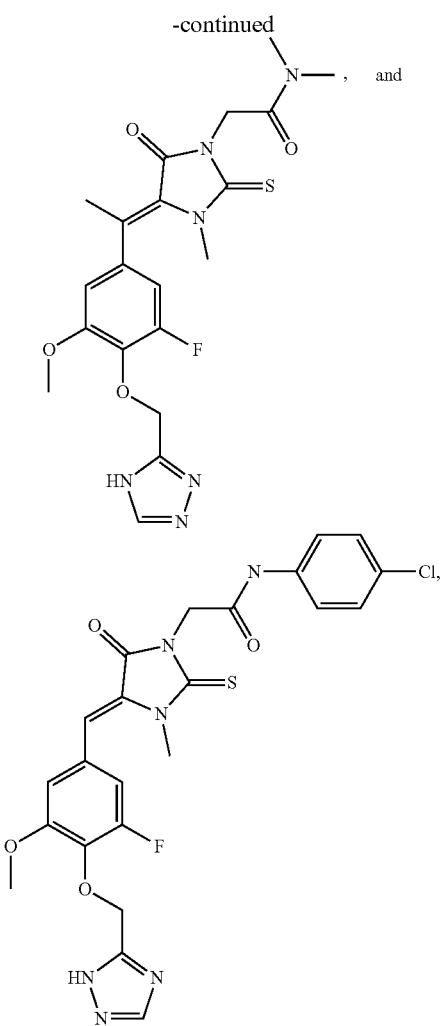

or a pharmaceutically acceptable salt thereof. In some embodiments, the disclosure provides a compound having a structure:

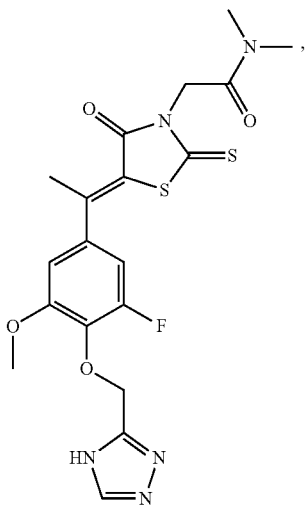 [SMILES: COc1cc(/C(C)=C2\SC(=S)N(CC(=O)N(C)C)C2=O)cc(F)c1OCc1nnc[nH]1]

or a pharmaceutically acceptable salt thereof.

Another aspect of the disclosure provides a pharmaceutical composition comprising the compound or salt described herein and a pharmaceutically acceptable excipient.

Yet another aspect of the disclosure provides a method of inhibiting the Notch transcriptional activation complex ("NTC") in a cell, comprising contacting the cell with a compound or salt described herein, or a composition described herein, in an amount effective to inhibit the NTC. In some embodiments, the compound inhibits MAML1 recruitment to the Notch transcriptional activation complex. In various embodiments, the contacting occurs in vivo. In some cases, the contacting comprises administering to a patient in need thereof. In various cases, the patient suffers from a disease associated with deregulation of the Notch transcriptional activation complex. In some embodiments, the disease is Tetralogy of Fallot ("TOF") or Alagille syndrome. In various embodiments, the disease is cancer. Contemplated cancers include a cancer selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), multiple sclerosis ("MS"), head and neck squamous cell carcinoma ("HNSCC"), renal cell adenocarcinoma, gastric and esophageal cancers, and fibrosarcoma.

Yet another aspect of the disclosure provides a method of treating Tetralogy of Fallot ("TOF") or Alagille syndrome comprising administering to a patient in need thereof a therapeutically effective amount of a compound or composition disclosed herein.

Still another aspect of the disclosure provides a method of treating cancer selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), multiple sclerosis ("MS"), head and neck squamous cell carcinoma ("HNSCC"), renal cell adenocarcinoma, gastric and esophageal cancers, and fibrosarcoma comprising administering to a patient in need thereof a therapeutically effective amount of a compound or composition of the disclosure.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE INVENTION

Figure 1A:
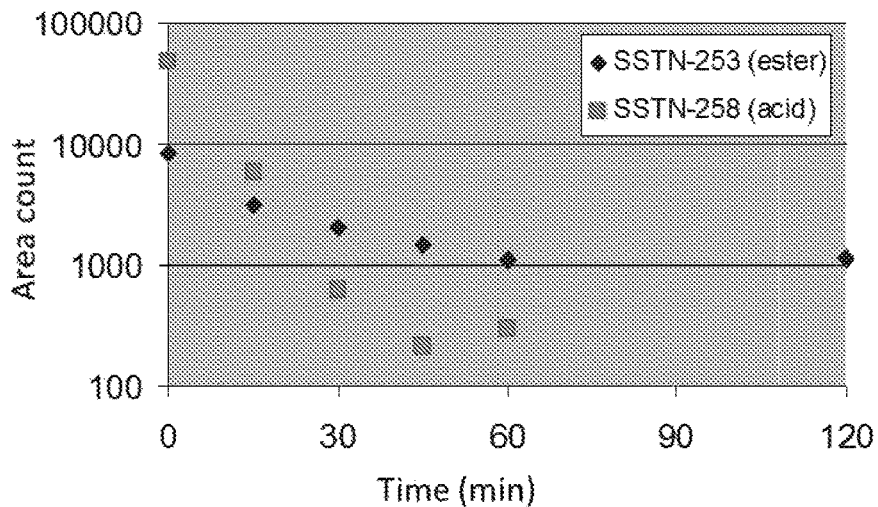
FIG. 1A depicts a graph showing the rapid metabolism of a potent NTC inhibitor (SSTN-253) via ester hydrolysis to its acid form (SSTN-258) in mouse hepatocytes.

Provided herein are compounds that inhibit the Notch transcriptional activation complex ("NTC"), and methods of using the compounds to decrease Notch target gene transcription, and to treat and prevent diseases associated with the NTC, such as cancer. The compounds disclosed herein have nanomolar potency, up to 100% bioavailability, and exhibit superior metabolic stability over previously disclosed Notch inhibitors.

Assembly of the Notch transcriptional activation complex is thought to occur in a stepwise fashion. Without being bound by any particular theory, the RAM domain of Notch and the β-trefoil domain ("BTD") of CSL form a high affinity interface. The Ankyrin repeat domain ("ANK") of Notch makes contacts with the C-terminal domain ("CTD") of CSL. Together, Notch and CSL create a cleft, which is required for stable MAML1 association to the complex. MAML1 interacts with the ANK domain of Notch, and also with both the N-terminal domain ("NTD") and CTD domains of CSL through an α-helical domain in its N-terminus. Once bound, MAML1 locks the core scaffold together and serves to recruit the higher order transcription regulatory machinery, thereby initiating the expression of Notch target genes.

Also without being bound by any particular theory, the compounds disclosed herein disrupt the recruitment of MAML1 to the Notch transcriptional activation complex on chromatin, thereby uncoupling the Notch mediated transcriptional cascade in response to activation, and decreasing Notch target gene transcription. As a result, the growth of Notch-dependent cells is inhibited, which stunts tumor growth in a subject. In some cases, the compounds disclosed herein are specific for Notch dependent cells, and therefore, do not inhibit or kill cells that are not dependent on Notch.

Notch is a particularly attractive target for inhibitor development. Prior to ligand activation and cleavage, the intracellular domain of Notch ("NICD") is bound to the cell membrane, and therefore, accessible to potential inhibitors. Further, the NTC is constantly being recycled, thus requiring constant reformation on chromatin for maintenance of the Notch transcriptional cascade driving the neoplastic phenotype. Therefore, ample opportunity exists for a small molecule to target the exposed interaction surfaces on the NTC components and prevent complex formation.

The compounds of the disclosure can inhibit formation of the NTC by more than about 50%, 55%, 60%, 65%, 70%, 75%, 80%, 85%, 90%, 95%, 97%, or 99% of the positive control. In some embodiments, the compounds of the disclosure can inhibit formation of the NTC by more than about 75%, 80%, 85%, 90%, 95%, 97%, or 99% of the positive control. For example, the compounds disclosed herein can inhibit formation of the NTC by more than about 85%, 86%, 87%, 88%, 89%, 90%, 91%, 92%, 93%, 94%, 95%, 96%, 97%, 98%, or 99% of the positive control. Furthermore, the compounds disclosed herein can disrupt the assembly of the NTC with an $IC_{50}$ of less than about 0.5 µM, or less than about 0.4 µM, or less than about 0.3 µM, or less than about 0.2 µM, or less than about 0.1 µM, or less than about 0.05 µM, or less than about 0.04 µM, or less than about 0.03 µM, or less than about 0.02 µM, or less than about 10 nM, or less than about 9 nM, or less than about 8 nM, or less than about 7 nM, or less than about 6 nM, or less than about 5 nM, or less than about 4 nM, or less than about 3 nM. In some cases, the compounds of the disclosure can disrupt the assembly of the NTC with an $IC_{50}$ of less than about 50 nM, or less than about 40 nM, or less than about 30 nM, or less than about 20 nM, or less than about 10 nM, or less than about 9 nM, or less than about 8 nM, or less than about 7 nM, or less than about 6 nM, or less than about 5 nM, or less than about 4 nM, or less than about 3 nM. In some cases, the compounds of the disclosure can disrupt the assembly of the NTC with an $IC_{50}$ of less than about 25 nM, or less than about 10 nM, or less than about 9 nM, or less than about 8 nM, or less than about 7 nM, or less than about 6 nM, or less than about 5 nM, or less than about 4 nM, or less than about 3 nM.

The compounds of the disclosure have several advantageous properties and effects. They can disrupt the assembly of the NTC with IC$_{50}$s in the nanomolar range. They can be 100% bioavailable. They can exhibit superior metabolic stability. They can decrease Notch target gene expression and selectively inhibit the formation of the Notch 1 transcription complex. They can inhibit tumor sphere viability and tumor growth. In addition, they do not exhibit the dose limiting toxicity of goblet cell metaplasia observed with pan notch inhibitors Notch Transcriptional Activation Complex ("NTC") Inhibitors.

Notch Transcriptional Activation Complex ("NTC") Inhibitors

Disclosed herein are compounds that can inhibit the Notch transcriptional activation complex with nanomolar potency, up to 100% bioavailability, and superior metabolic stability over previously disclosed Notch inhibitors.

In some embodiments the compounds include a compound of Formula (I), or a pharmaceutically acceptable salt thereof:

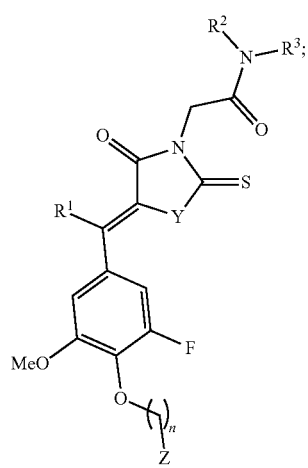

wherein n is 1 or 2; Y is O, S, or NC$_{1-3}$alkyl; Z is triazolyl; R$^1$ is H or C$_{1-3}$alkyl; R$^2$ is H or C$_{1-3}$alkyl; and R$^3$ is C$_{1-3}$alkyl or halophenyl.

As used herein, the term "alkyl" refers to straight chained and branched saturated hydrocarbon groups containing one to thirty carbon atoms, for example, one to twenty carbon atoms, or one to ten carbon atoms. The term Cn means the alkyl group has "n" carbon atoms. For example, C$_4$ alkyl refers to an alkyl group that has 4 carbon atoms. C$_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "halophenyl" refers to a phenyl group,

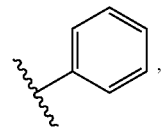

having one or more halogen substituents, such as fluoro, chloro, bromo, or iodo. In some cases, the halophenyl group has one halogen substituent,

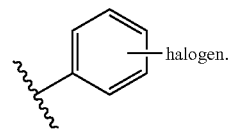

The halogen substituent can be ortho-, metha-, or para-substituted.

In some embodiments, n is 1. In various embodiments, n is 2.

In some embodiments, Y is O. In some cases, Y is S. In various cases, Y is NC$_{1-3}$alkyl. In various embodiments, Y is NCH$_3$.

In various cases, Z is a 1,2,4-triazolyl. In some embodiments, Z is a 1,2,3-triazolyl. In some cases, Z is selected from the group consisting of

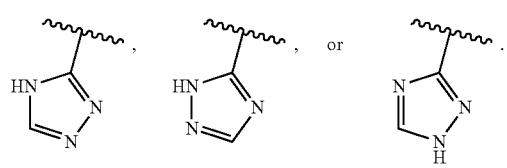 [SMILES: *c1nnc[nH]1 ; *c1ncn[nH]1 ; *c1nc[nH]n1]

In various embodiments, Z is

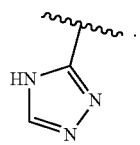

In various embodiments, Z is

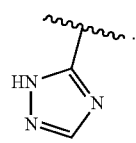

In various embodiments, Z is

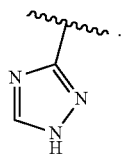

In some embodiments, $R^1$ is H. In some cases, $R^1$ is selected from the group consisting of methyl, ethyl, propyl, and isopropyl. In various embodiments, $R^1$ is $CH_3$.

In some cases, $R^2$ is H. In some embodiments, $R^2$ is selected from the group consisting of methyl, ethyl, propyl, and isopropyl. In various cases, $R^2$ is $CH_3$. In some embodiments $R^3$ is $CH_3$. In some cases, $R^3$ is selected from the group consisting of fluorophenyl, chlorophenyl, bromophenyl, and iodophenyl. In some embodiments, $R^3$ is fluorophenyl, chlorophenyl, or bromophenyl. In some cases, $R^3$ is fluorophenyl. In various cases, $R^3$ is bromophenyl, In various embodiments, $R^3$ is chlorophenyl. In some embodiments, $R^3$ is para-chlorophenyl. In some cases, $R^2$ is $CH_3$ and $R^3$ is $CH_3$. In various cases, $R^2$ is H and $R^3$ is chlorophenyl (e.g., para-chlorophenyl). In various cases, $R^2$ is $CH_3$ and $R^3$ is chlorophenyl (e.g., para-chlorophenyl).

In some embodiments, n is 1; Y is S; $R^1$ is $CH_3$; $R^2$ is $CH_3$; and $R^3$ is $CH_3$, as shown in Formula (I'), below:

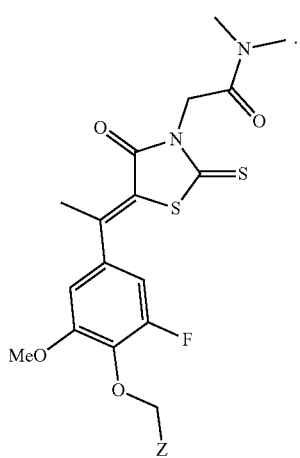

(I')

Contemplated compounds of the disclosure include compounds of Table A, below:

TABLE A

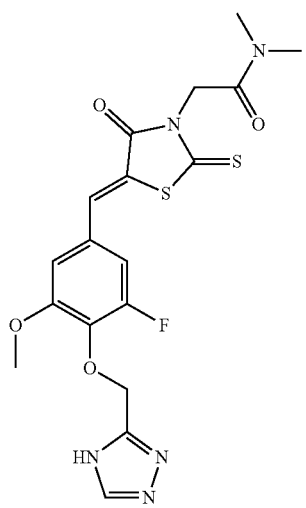

NADi-260
Example #1

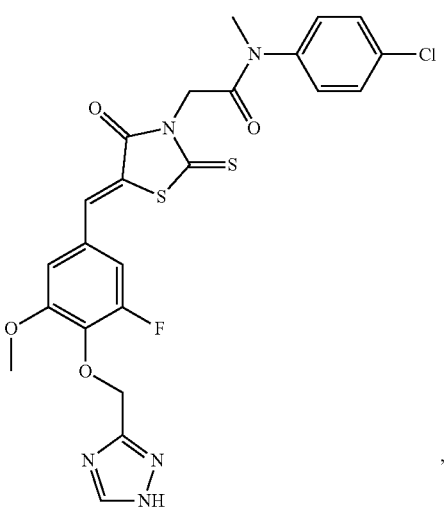

NADi-327
Example #2

TABLE A-continued
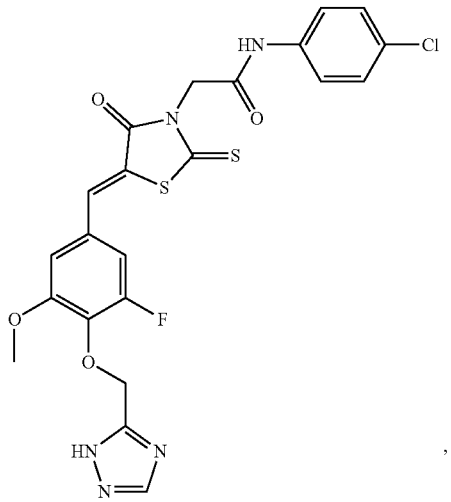
NADi-333
Example #3
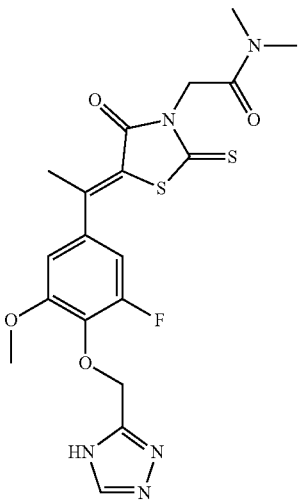
NADi-351
Example #5
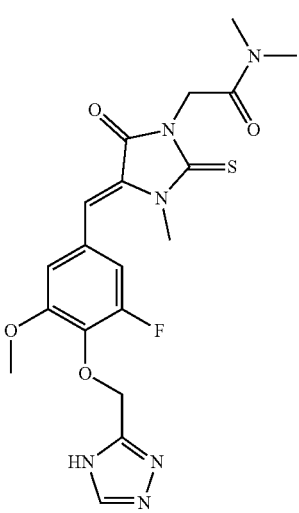
NADi-335
Example #4
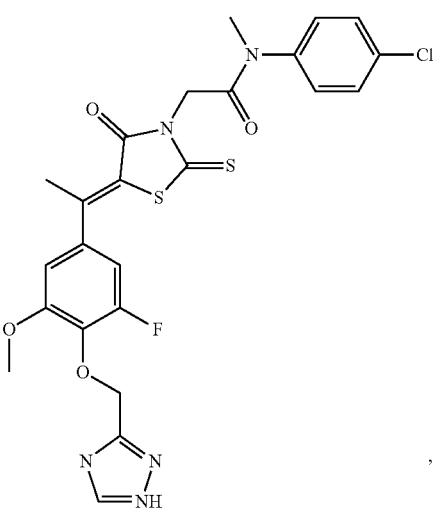
NADi-355
Example #6

TABLE A-continued

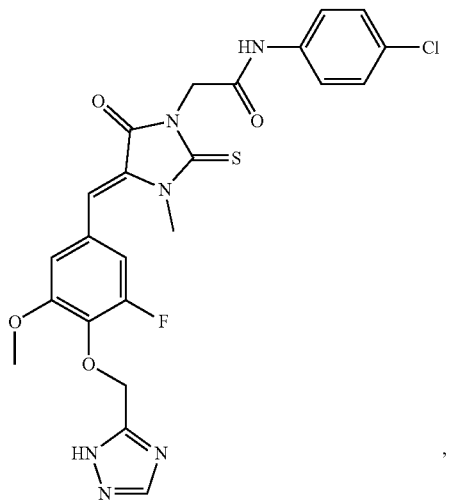

NADi-359
Example #7 and

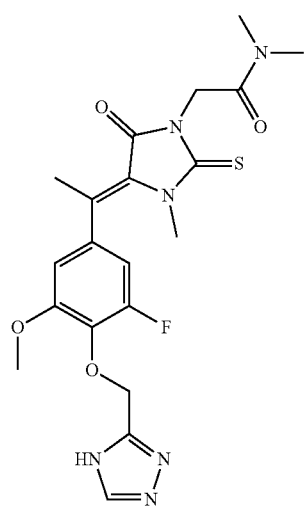

NADi-374.

In some embodiments, provided herein is a compound having a structure:

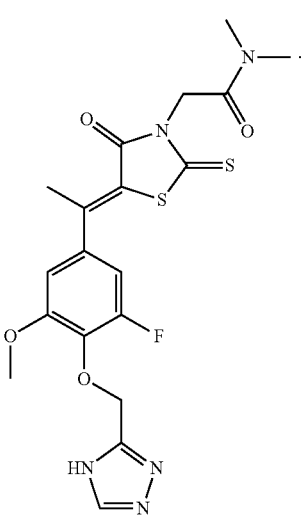

(NADi-351)

As previously described, the compounds of the disclosure can exhibit nanomolar potency, up to 100% bioavailability, and superior metabolic stability over previously disclosed Notch inhibitors.

Without intending to be bound by any particular theory, the combination of the methoxy and fluoro groups on the phenyl ring, as well as the amide group on the thiazolidinone ring,

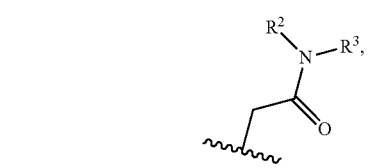

result in improved potency of the Notch inhibitors because each of the specific functional groups allow for increased cell permeability. For example, compounds having the structure, below:

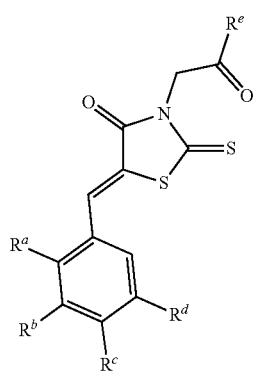

with $R^b$ as $OCH_3$, $R^d$ as F, and $R^e$ as $CH_2CON(CH_3)_2$, exhibit a significantly improved $IC_{50}$ for the NTC over other compounds that do not have the specific combination of substituents. See Table B, below, specifically SSTN-253.

TABLE B

| Cmpd # | R[a] | R[b] | R[c] | R[d] | R[e] | IC$_{50}$ (μM) NTC | Cell viability (MTT, μM, 72 h treatment OE 33 cell line) |
|---|---|---|---|---|---|---|---|
| SSTN-247 | H | OMe | OCH$_2$CO$_2$Et | H | CH$_2$CO$_2$H | 2.2 | >25 |
| SSTN-248 | H | OEt | OCH$_2$CO$_2$Et | H | H | 44.5 | 23.5 |
| SSTN-249 | OCH$_2$CO$_2$Et | H | H | F | H | 14.2 | >25 |
| SSTN-250 | H | OMe | OCH$_2$CO$_2$Et | H | CH$_2$CONMe$_2$ | 0.6 | 10.5 |
| SSTN-251 | OCH$_2$CO$_2$Et | H | H | F | CH$_2$CONMe$_2$ | 5.1 | 12.8 |
| SSTN-252 | H | OMe | OCH$_2$CO$_2$Et | F | H | 39.6 | 16.8 |
| SSTN-253 | H | OMe | OCH$_2$CO$_2$Et | F | CH$_2$CONMe$_2$ | 0.058 | 9.3 |
| SSTN-258 | H | OMe | OCH$_2$CO$_2$H | F | CH$_2$CONMe$_2$ | Inactive | No effect |
| SSTN-254 | H | OMe | OCH$_2$CO$_2$H | H | CH$_2$CONMe$_2$ | 4.4 | >25 |
| SSTN-255 | H | OEt | OCH$_2$CO$_2$H | H | H | 5.2 | >25 |
| SSTN-256 | OCH$_2$CO$_2$H | H | H | F | H | 7.7 | >25 |
| SSTN-257 | H | OMe | OCH$_2$CO$_2$H | F | H | 5.8 | >25 |

Figure 1B:
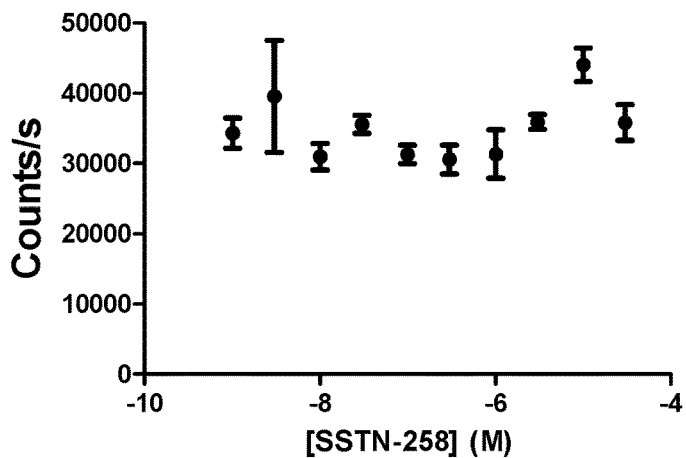
FIG. 1B depicts a graph showing that acid metabolite, SSTN-258, does not inhibit the NTC assembly, as determined with the NTC AlphaScreen assay.
Figure 1C:
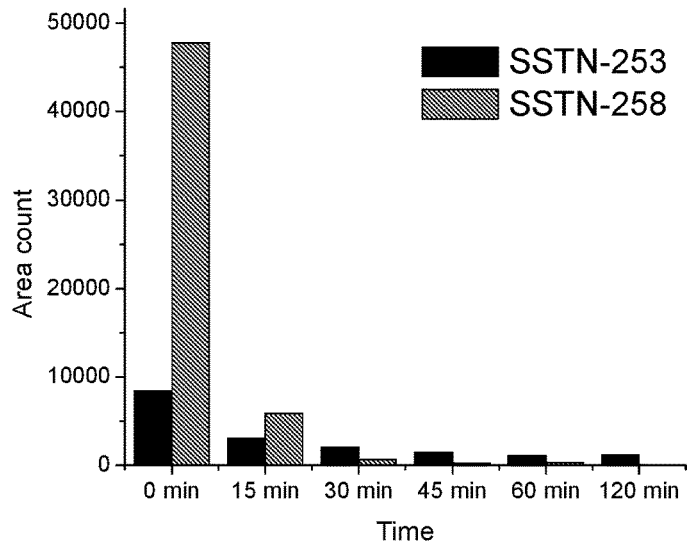
FIG. 1C depicts a graph showing the results of a pharmacokinetic study of SSTN-253 in mouse plasma. The study demonstrated that SSTN-253 metabolizes to its acid form (SSTN-258) in mouse plasma, with subsequent metabolism observed.

Also without being bound by any particular theory, compounds having a OCH$_2$-triazolyl group on the phenyl ring para to the alkene exhibit increased metabolic stability because they are not susceptible to hydrolysis. For example, despite having superior potency, SSTN-253 was found to rapidly metabolize (within 15 minutes) to its acid form (i.e., to SSTN-258 in Table B) in mouse hepatocytes (see FIG. 1A and FIG. 1C) and liver microsomes. The acid metabolite (SSTN-258) did not inhibit the NTC assembly (see FIG. 1B).

When the ester moiety of SSTN-253 is substituted with a triazolyl moiety, an increase in metabolic stability results, while superior potency is maintained. As shown in Table C, below, compounds having a triazolyl group at R (NADi-260 to NADi-262), exhibit an IC$_{50}$ as low as 20 nm.

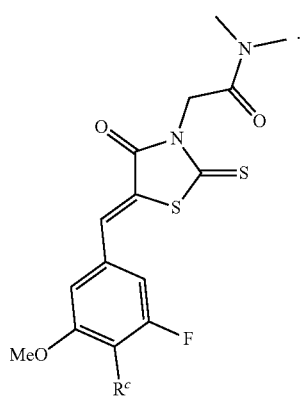

TABLE C

| Cmpd# | R[c] | *IC$_{50}$ (μM) |
|---|---|---|
| SSTN-253 | (OCH$_2$C(O)OEt) | 0.06 |
| NADi-244 | (OCH$_2$C(O)NEt$_2$) | 2.9 |

TABLE C-continued

| Cmpd# | R[c] | *IC$_{50}$ (μM) |
|---|---|---|
| NADi-248 | (OCH$_2$-oxazole) | Inactive |
| NADi-249 | (OCH$_2$-5-methyloxazole) | Inactive |
| NADi-251 | (OCH$_2$-4,5-dimethyloxazole) | Inactive |
| NADi-252 | (OCH$_2$-5-ethyloxazole) | Not determined** |
| NADi-253 | (OCH$_2$-4-ethyloxazole) | 0.3*** |
| NADi-255 | (OCH$_2$-5-methyl-1,3,4-oxadiazole) | Inactive |
| NADi-256 | (OCH$_2$-5-ethyl-1,3,4-oxadiazole) | Inactive |

TABLE C-continued

| Cmpd# | R$^c$ | *IC$_{50}$ (μM) |
|---|---|---|
| NADi-258 | 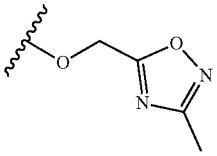 [SMILES: *OCc1nc(C)no1] | Inactive |
| NADi-259 | 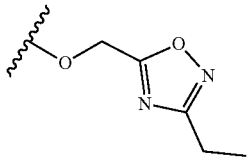 [SMILES: *OCc1nc(CC)no1] | Inactive |
| NADi-260 | 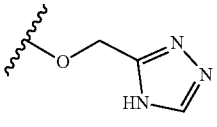 [SMILES: *OCc1nnc[nH]1] | 0.02 |
| NADi-261 | 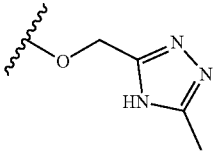 [SMILES: *OCc1nnc(C)[nH]1] | 0.62 |
| NADi-262 | 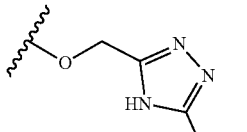 | 0.08 |

Figure 2:
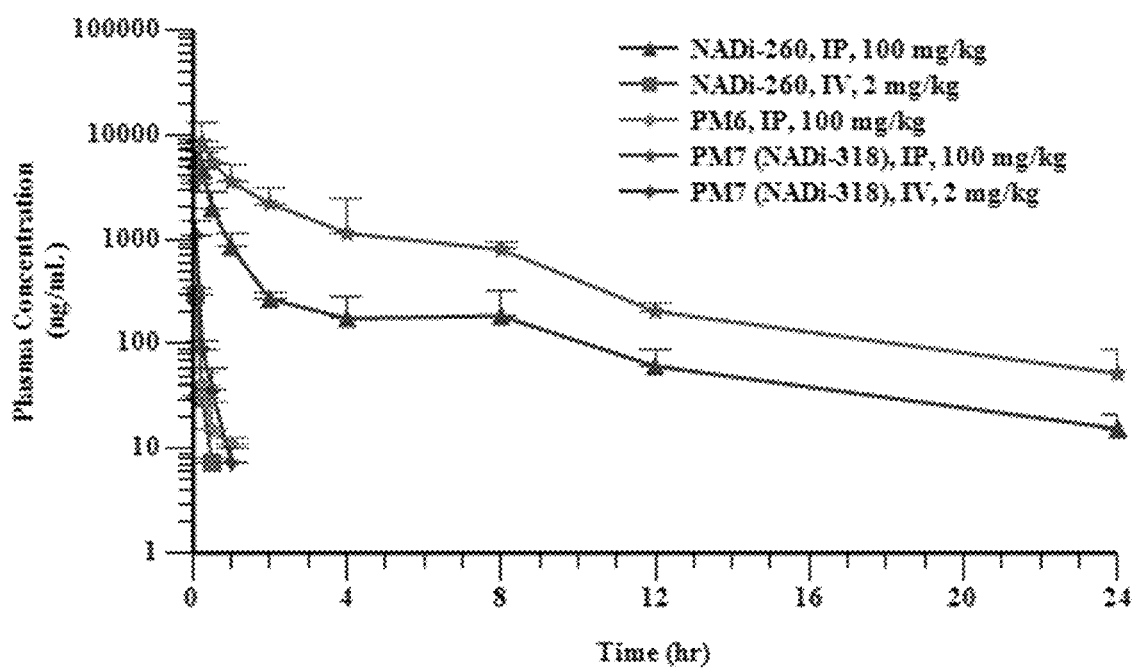
FIG. 2 depicts the mean plasma concentration-time profiles of NADi-260 and its main metabolites PM6 (resulting from the dealkylation of the methyl triazole to give the corresponding phenol) and PM7 (reduction product) in mouse plasma. NADi-260 was administered by intraperitoneal (i.p.) and intravenous (i.v.) routes.

*IC50 values determined via the NTC AlphaScreen assay
**low solubility in DMSO
***high variability in data set Table D, below, shows the pharmacokinetic parameters for NADi-260, and its main metabolites PM6 (resulting from dealkylation of the terminal oxygen) and PM7 (resulting from reduction of the alkene), in mouse plasma. The data indicate improvement of metabolic stability upon replacement of the ester moiety at R$^c$ with a triazolyl group. See also, FIG. 2, which depicts the mean plasma concentration-time profiles of NADi-260 and its main metabolites after intraperitoneal and intravenous administration.

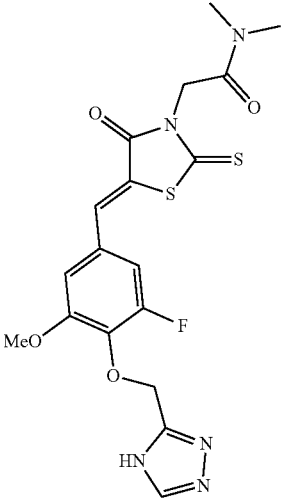

NADi-260

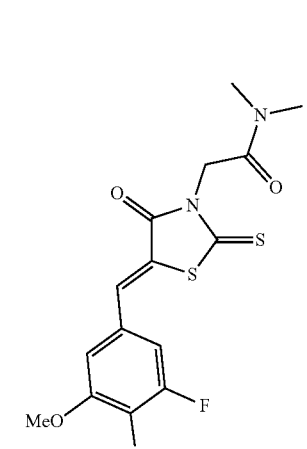

PM6

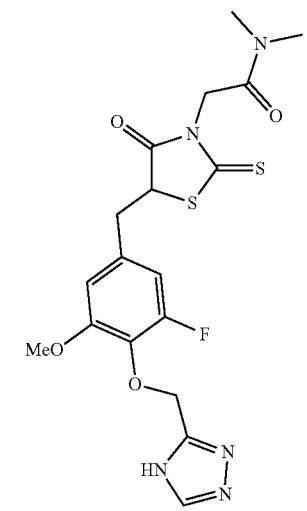

PM7

TABLE D

| Cmpd# | Route | Dose (mg/kg) | $T_{max}$ (hr) | *$C_0/C_{max}$ (ng/mL) | $AUC_{last}$ (hr*ng/mL) | $AUC_{inf}$ (hr*ng/mL) | $T_{1/2}$ (hr) | CL (mL/min/kg) | $V_{ss}$ (L/kg) |
|---|---|---|---|---|---|---|---|---|---|
| NADi-260 | i.v.** | 2 | — | 837 | 77 | 78 | 0.08 | NR | 1.79 |
|  | i.p. | 100 | 0.08 | 5695 | 5322 | 5424 | — | — |  |
| PM6 | i.v. | — | BQL |  |  |  |  |  |  |
|  | i.p. | — | 0.25 | 41 | 21 | NC | — | — |  |
| PM7 | i.v. | — | — | 3479 | 308 | 310 | — | — |  |
|  | i.p. | — | 0.25 | 8519 | 18760 | 19063 | — | — |  |

*back extrapolated value for i.v. route
**PK parameters were calculated using available data of initial three time points only (0.08, 0.25 and 0.5 h)
NR: not reportable due to high clearance value (Cl mL/min/kg = 428.52)
BQL—Below quantification limit
NC—Not calculated (insufficient data points)

Figure 3:
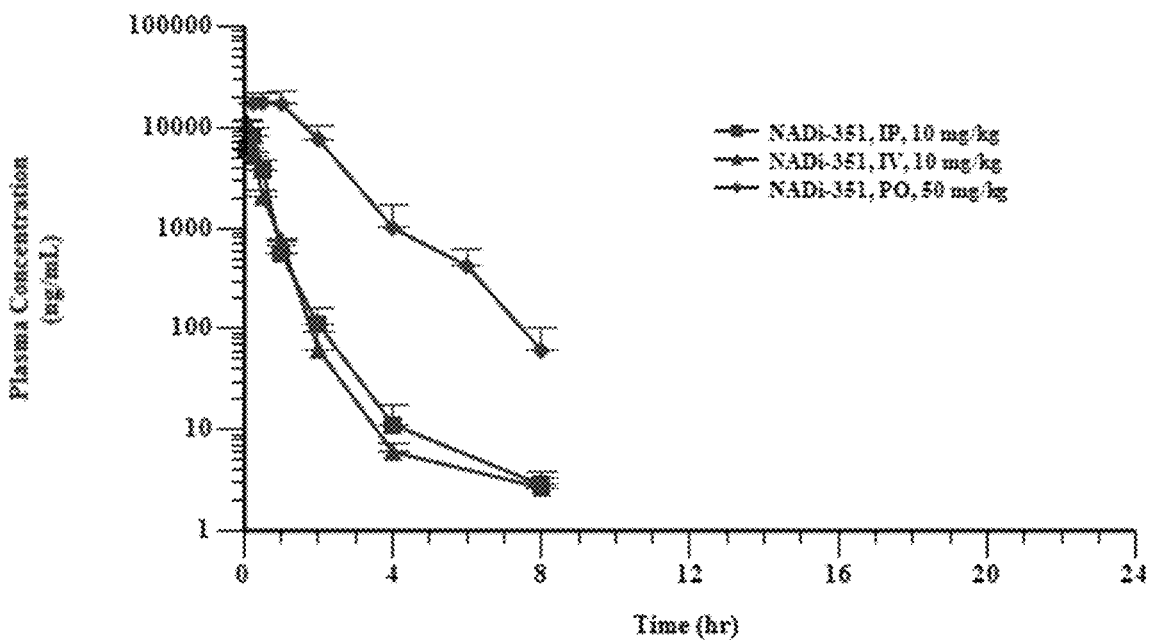
FIG. 3 depicts a pharmacokinetic profile of NADi-351 in mouse plasma, demonstrating that NADi-351 exhibits improved metabolic stability over NADi-260 and excellent oral bioavailability.

Also without intending to be bound by any particular theory, the presence of a methyl group on the alkene results in compounds having improved potency, improved metabolic stability, and excellent oral bioavailability over compounds that do not have a methylated alkene. For example, when NADi-260 was methylated at the alkene, the potency of the resulting compound (NADi-351) increased by 10-fold with significantly improved metabolic stability and excellent bioavailability. See FIG. 3 and Table E.

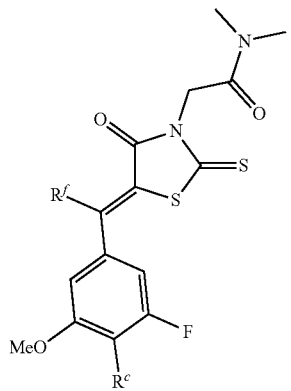

TABLE E

| Cmpd# | $R^c$ | $R^f$ | *$IC_{50}$ (nM) |
|---|---|---|---|
| SSTN-253 | (ethyl ester -O-CH2-C(=O)-O-Et) | H | 60 |
| NADi-260 | (-O-CH2-triazole) | H | 20 |
| NADi-351 | (-O-CH2-triazole) | $CH_3$ | 2.4 |

*$IC_{50}$ values determined via the NTC AlphaScreen assay

Furthermore, a pharmacokinetic study of NADi-351 in mouse plasma following a single intravenous (10 mg/kg), intraperitoneal (10 mg/kg) and oral (50 mg/g) administration also indicated improvement of metabolic stability when compared to the unmethylated NADi-260, as shown in Table F, below.

TABLE F

| Cmpd# | Route | Dose (mg/kg) | $T_{max}$ (hr) | *$C_0/C_{max}$ (ng/mL) | $AUC_{last}$ (h*ng/mL) | $AUC_{inf}$ (h*ng/mL) | $T_{1/2}$ (hr) | CL (mL/min/kg) | $V_{ss}$ (L/kg) | % F |
|---|---|---|---|---|---|---|---|---|---|---|
| NADi-351 | i.v. | 10 | — | 15948 | 4567 | 4571 | 1.46 | 36.46 | 0.80 | — |
|  | i.p. | 10 | 0.25 | 8198 | 4547 | 4550 | — | — | — |  |
|  | p.o. | 50 | 0.50 | 17528 | 37927 | 38032 | — | — | — | >100 |

*back extrapolated value for i.v. route

Without intending to be bound by any particular theory, the presence of the methyl group on the alkene results in superior metabolic stability because it decreases Michael receptor reactivity at the alkene by blocking glutathione conjugation. For example, when NADi-260 and NADi-351 were each reacted with glutathione ("GSH"), NADi-260 showed GSH ethyl ester conjugation within 60 minutes of incubation in human liver microsomes ("HLM"), but NADi-351 showed increased stability toward GSH ethyl ester conjugation in HLM during that time. See Table G, below.

TABLE G

| Cmpd # | Incubation Time (min) | Percentage (%) Parent Remaining in HLM |
|---|---|---|
| NADi-260 | 0 | 100 |
| | 60 | 46 |
| NADi-351 | 0 | 100 |
| | 60 | 86 |

The compounds disclosed herein also exhibit excellent aqueous solubility. For example, the aqueous solubility of NADi-351 in simulated gastric fluid ("SGF") at pH 1.2 and fasted-state simulated intestinal fluid ("FaSSIF") at pH 6.5 was determined and compared to the positive controls, omeprazole and chlorambucil. The aqueous solubility of NADi-351 in phosphate buffered saline ("PBS") at pH 7.4 was determined and compared to positive controls caffeine and diethylstilbestrol ("DES"). As shown in Table H and Table I, below, NADi-351 showed superior aqueous solubility over omeprazole, chlorambucil, and DES and similar aqueous solubility to caffeine.

TABLE H

| Compound | Solubility in SGF (µM) | Solubility in FaSSIF (µM) |
|---|---|---|
| Omeprazole (control) | <5 | 173.6 ± 5.4 |
| Chlorambucil (control) | 70.4 ± 2.6 | 68.9 ± 1.9 |
| NADi-351 | 157.5 ± 7.7 | 150.2 ± 4.1 |

TABLE I

| Compound | Solubility in PBS (µM) |
|---|---|
| Caffeine (control) | 157.9 ± 2.7 |
| DES (control) | <5 |
| NADi-351 | 154.7 ± 9.6 |

The compounds disclosed herein are relatively hydrophilic with clogP values in the 0-2 range. Incorporation of the chlorophenyl produces a significant increase in lipophilicity (clogP 2-3 range) which is likely to impart better ADMET (absorption, distribution, metabolism, elimination, and toxicity) properties.

Synthesis of the NTC Inhibitors

The compounds of the disclosure can be synthesized by any method known to one skilled in the art. For example, an appropriate aldehyde or methyl ketone group and an appropriate heterocycloalkyl group can undergo a condensation reaction under acidic or basic conditions, at an elevated temperature, to form the desired compounds, as shown in the scheme below.

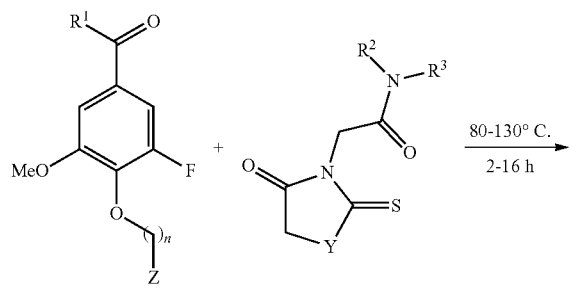

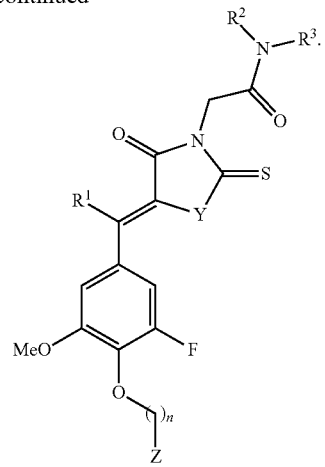

Additional synthetic procedures for preparing the compounds disclosed herein can be found in the Examples section.

Methods of Using the NTC Inhibitors

The compounds of the disclosure can inhibit the Notch transcriptional activation complex ("NTC") by disrupting recruitment of MAML1 to the complex, which is useful in preventing or treating diseases associated with deregulation of the Notch transcriptional activation complex. As used herein, the term "Notch transcriptional activation complex" ("NTC") refers to a complex of three proteins, the DNA binding protein CSL, the intracellular domain of Notch ("NICD") and the co-activator protein Mastermind ("MAML1"), which functions to activate transcription of target genes.

As previously described herein, the Notch pathway is restricted to small populations of progenitor and stem cells of regenerating tissues, such as the colon and brain. However, in many human cancers, the Notch pathway becomes reactivated, and this deregulation of the Notch pathway underlies many aspects of cancer physiology, depending on cell type and context.

Therefore, one aspect of the disclosure relates to a method of inhibiting the Notch transcriptional activation complex in a cell, comprising contacting the cell with a compound, or pharmaceutically acceptable salt of Formula (I), a compound listed in Table A, NADi-351, or a combination thereof, in an amount effective to inhibit the NTC. As used herein, the term "pharmaceutically acceptable" means that the referenced substance, such as a compound of the present invention or a composition containing the compound, or a particular excipient, are safe and suitable for administration to a subject or patient.

The compounds disclosed herein can inhibit the NTC in a cell by contacting the cell in vitro or in vivo. In some embodiments, the contacting occurs in vitro. In other embodiments, the contacting occurs in vivo. The compounds can contact the NTC in vivo by administering the compound to a subject or patient in need of regulation of the NTC. As used herein, the terms "patient" and "subject" may be used interchangeably and mean animals, such as dogs, cats, cows, horses, and sheep (i.e., non-human animals) and humans. Particular patients are mammals (e.g., humans). Put another way, in various embodiments, the invention includes administering one or more compounds of the disclosure to a subject or patient, such as a human, in need thereof. In some of these embodiments, the patient suffers from a disease associated with deregulation of the Notch transcriptional activation complex (e.g., Tetralogy of Fallot ("TOF"), Alagille syndrome, or cancer).

Another aspect of the disclosure relates to a method of treating a disease associated with deregulation of the Notch transcriptional activation complex in a patient, comprising administering to the patient a therapeutically effective amount of a compound or pharmaceutically acceptable salt of Formula (I), a compound listed in Table A, NADi-351, or a combination thereof. As used herein, the phrase "deregulation of the Notch transcriptional activation complex" or "deregulation of the NTC" refers to an abnormality in the regulatory ability of the NTC, resulting in reactivation of gene transcription. As used herein, the term "therapeutically effective amount" refers to an amount of a compound or combination of therapeutically active compounds (e.g., a compound described herein, or a combination of compounds) that ameliorates, attenuates or eliminates one or more symptoms of a particular disease or condition (e.g., cancer), or prevents or delays the onset of one of more symptoms of a particular disease or condition. As used herein the terms "treating", "treat" or "treatment" and the like include preventative (e.g., prophylactic) and palliative treatment. In some embodiments, the disease is selected from Tetralogy of Fallot ("TOF"), or Alagille syndrome. In some cases, the disease is cancer. In various embodiments, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, esophageal and gastric cancers, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), multiple sclerosis ("MS"), head and neck squamous cell carcinoma ("HNSCC"), renal cell adenocarcinoma, fibrosarcoma, and combinations thereof.

Use of a compound disclosed herein, or a pharmaceutically acceptable salt thereof, such as a compound of Formula (I), a compound listed in Table A, NADi-351, or a combination thereof, to treat a condition resulting from deregulation of the Notch transcriptional activation complex in a patient, as well as use of the inhibitor in the preparation of a medicament for treating the condition, also are contemplated.

The compounds disclosed herein can abrogate tumor growth through selective inhibition of Notch1 recruitment to the Notch ternary complex.

Figure 4A:
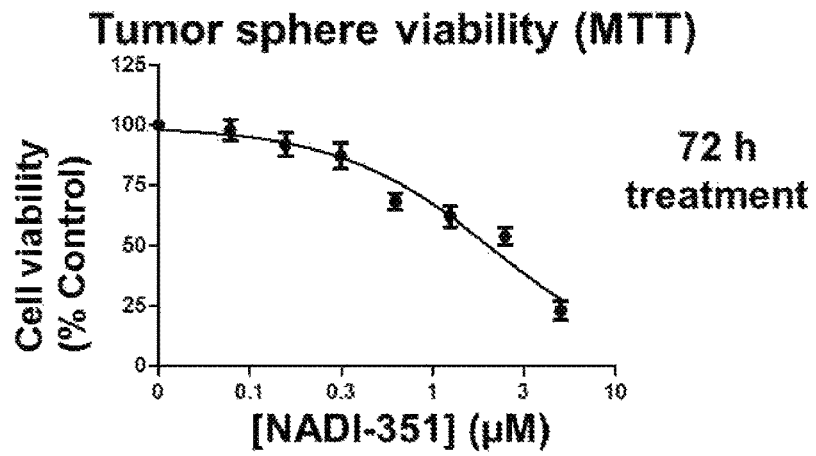
FIG. 4A depicts a graph showing the ability of NADi-351 to inhibit the tumor sphere viability of the OE33 cell line (esophageal adenocarcinoma) after 72 hours of treatment using the Methylthiazolyldiphenyl-tetrazolium bromide ("MTT") assay.
Figure 4B:
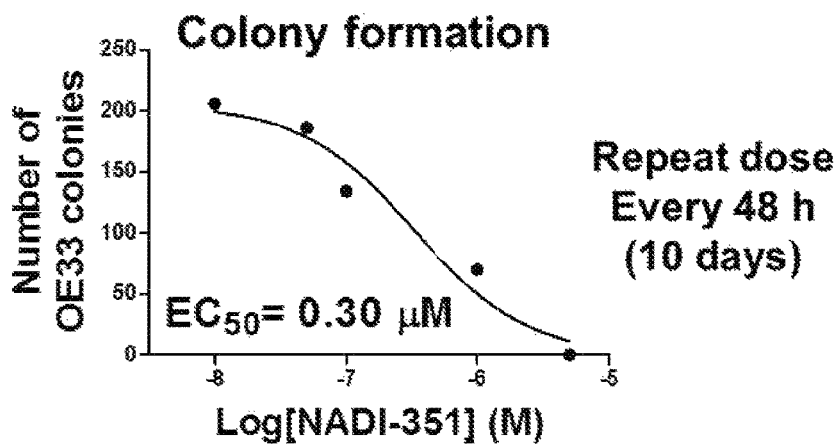
FIG. 4B depicts a graph showing the ability of NADi-351 to inhibit colony formation of the OE33 cell line (esophageal adenocarcinoma) after administering a repeat dose every 48 hours for 10 days.
Figure 4C:
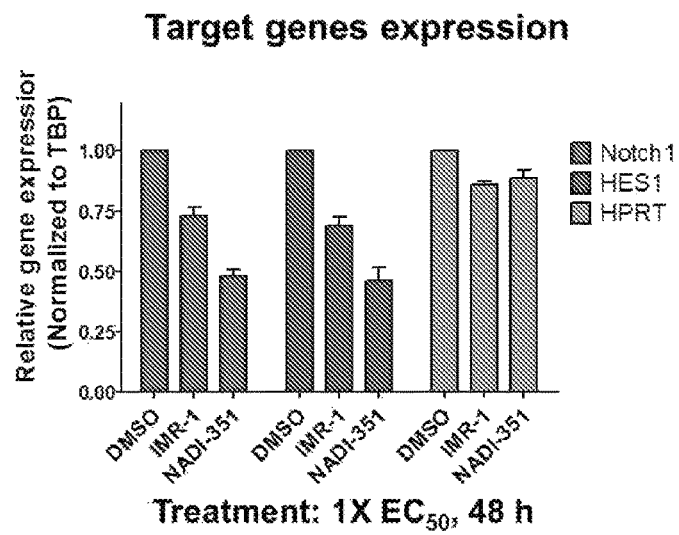
FIG. 4C depicts a graph showing the ability of NADi-351 to decrease Notch target gene expression after 48 h of treatment, compared to control (vehicle, DMSO). Data were normalized to housekeeping gene TBP.

The compounds and salts disclosed herein can inhibit the viability of tumor spheres and decrease Notch target gene expression. For example, as shown in FIG. 4A and FIG. 4B, NADi-351 decreased tumor sphere viability of the OE33 cell line (esophageal adenocarcinoma) by about 75% after 72 hours of treatment using the MTT assay, and decreased colony formation of the OE33 cell line using a repeat dose every 48 hours for 10 days. As shown in FIG. 4C, NADi-351 decreased the expression of Notch target genes compared to control.

Figure 5A:
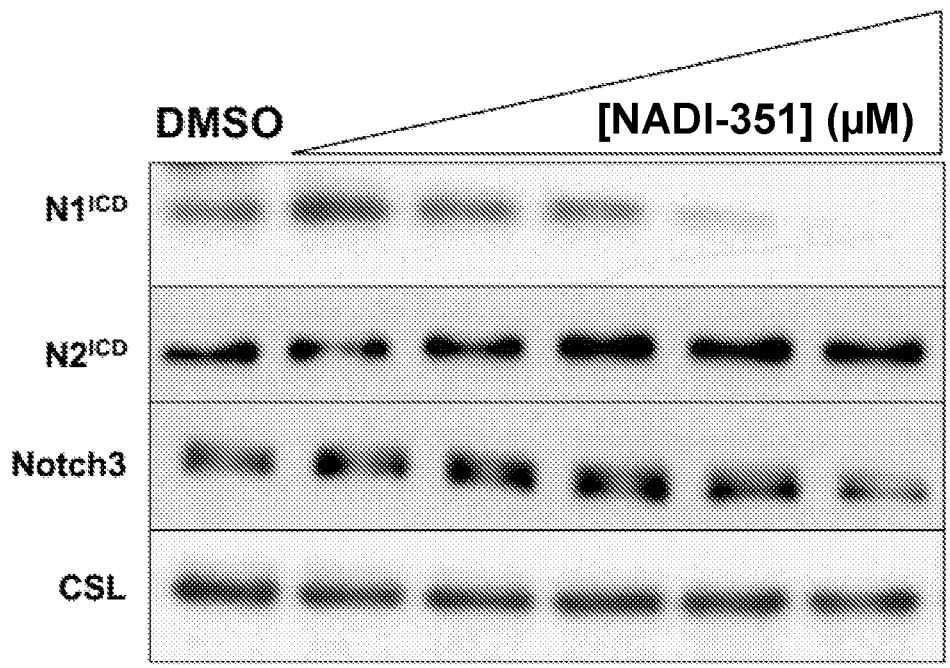
FIG. 5A depicts the results of a 2×CSL DNA affinity precipitation using the nuclear lysate of OE33 cell line (esophageal adenocarcinoma). Cells were treated with either vehicle (DMSO) or NADi-351 for 48 h. Analysis of the DNA affinity precipitation indicate that NADi-351 selectively inhibits the formation of the Notch1 transcriptional complex over Notch2, Notch3, and CSL in a dose-dependent manner.
Figure 5B:
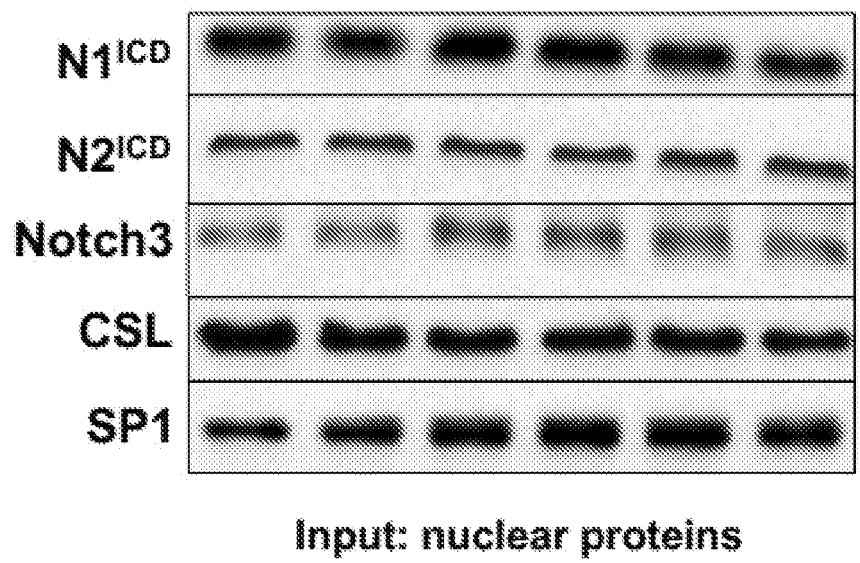
FIG. 5B demonstrates that when nuclear proteins are subjected to the 2×CSL DNA affinity precipitation analysis described in FIG. 5A, that the Notch1 transcriptional complex is not inhibited.

The compounds and salts disclosed herein can selectively inhibit the formation of the Notch 1 transcriptional complex. For example, as shown in FIGS. 5A and 5B, compared to control, NADi-351 inhibited the formation of the Notch1 intracellular domain ($N1^{icd}$), but not the Notch2 intracellular domain ($N2^{icd}$), Notch 3, or CSL, after 48 hours of treatment using the OE33 cell line (esophageal adenocarcinoma) (FIG. 5A).

Figure 6A:
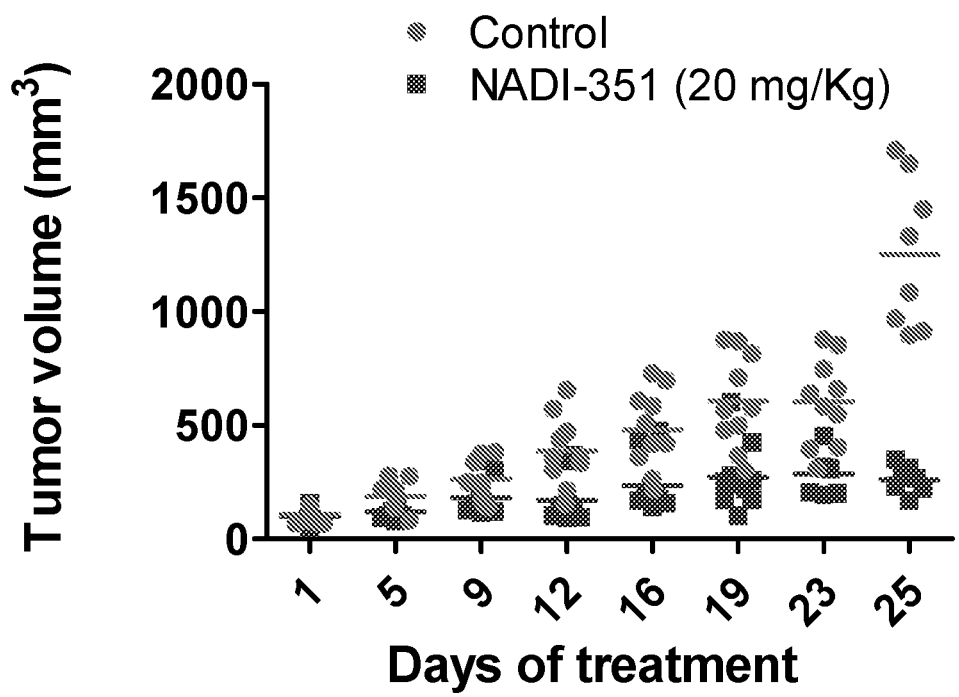
FIG. 6 depicts the effect of NADi-351 on tumor growth in an esophageal adenocarcinoma patient-derived xenograft ("PDX") model. Over 25 days of treatment, the volume of tumors treated with NADi-351 were significantly reduced compared to control (FIG. 6A), while the body weight of the subjects were substantially maintained (FIG. 6B).
Figure 6B:
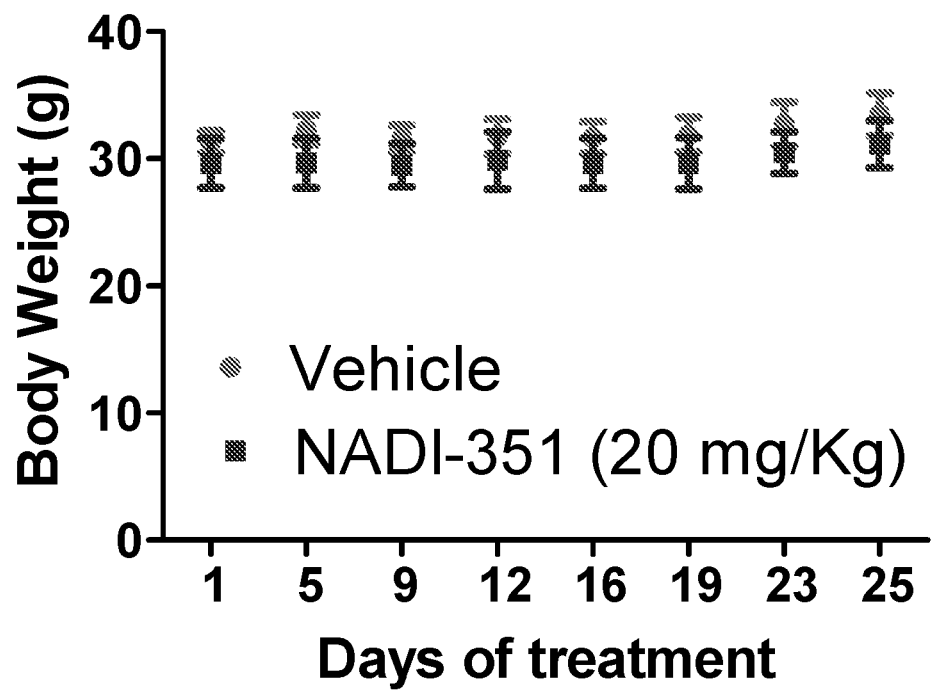

The compounds and salts disclosed herein can reduce tumor volume while maintaining body weight in esophageal adenocarcinoma patient-derived xenograft ("PDX") models. When tumors (250 mm$^3$) that were established in NSG mice were exposed to NADi-351 over 25 days of treatment, the volume of the tumor was significantly inhibited compared to control (see FIG. 6A), but the body weight of the subjects remained constant (see FIG. 6B).

Figure 7:
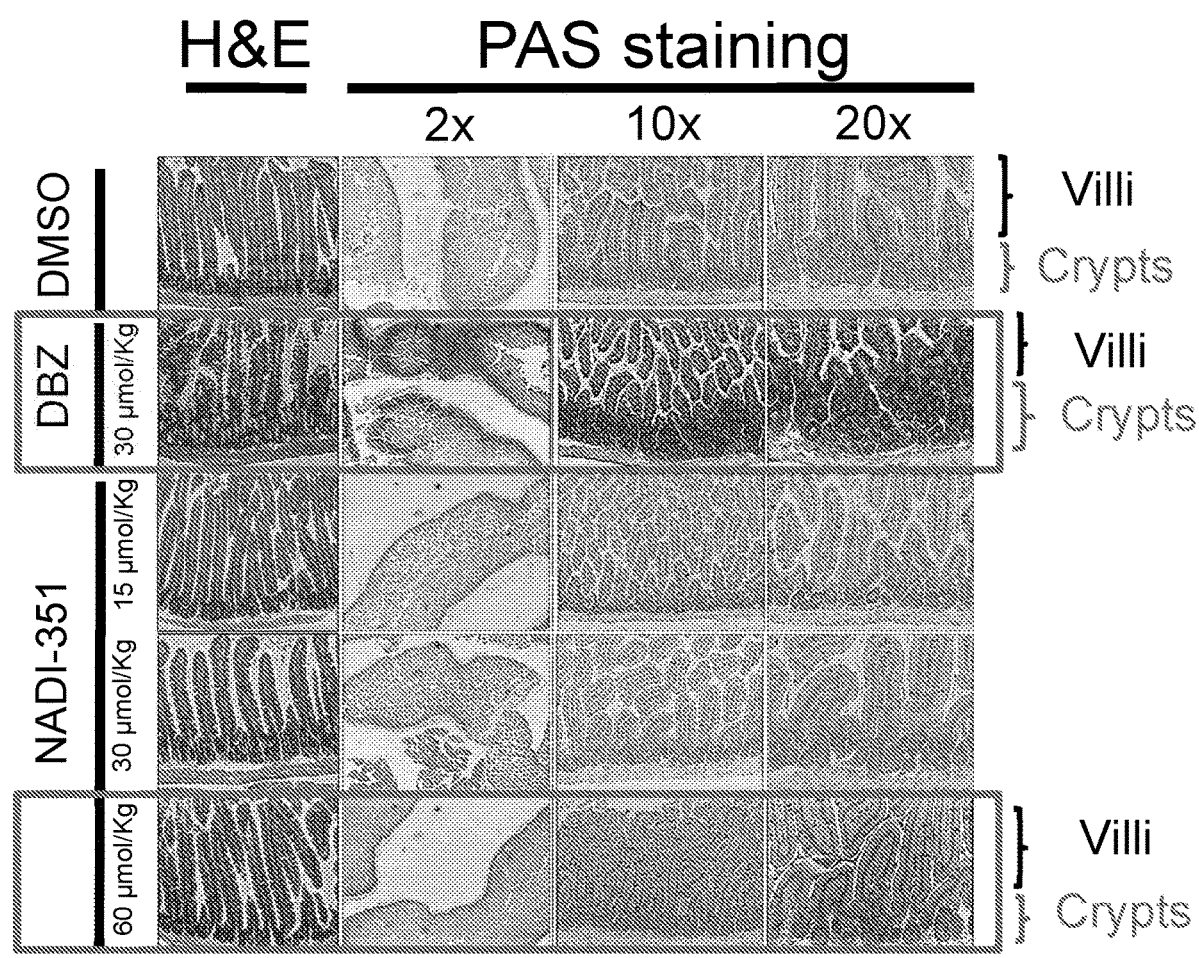
FIG. 7 depicts the results of H&E and PAS staining of intestinal crypts exposed to control (DMSO), an efficacious dose of dibenzazepine ("DBZ"), a γ-secretase inhibitor, and 4× the efficacious dose of NADi-351 for 5 days. The DBZ-treated sample showed a vast amount of PAS staining at low magnification and complete disruption of crypts at high magnification (PAS Staining indicative of goblet cell metaplasia in crypts). In contrast, NADi-351 showed no goblet cell metaplasia and intact crypts, comparable to the control group.

The compounds and salts disclosed herein no not induce goblet cell metaplasia in intestinal crypts. Intestinal crypts were exposed to vehicle (DMSO), an efficacious dose of dibenzazepine ("DBZ"), a γ-secretase inhibitor, and 4× the efficacious dose of NADi-351 and stained with a hemotoxylin and eosin ("H&E") stain and a periodic acid-Schiff ("PAS") stain. The DBZ-treated sample showed a vast amount of PAS staining at low magnification and complete disruption of crypts at high magnification. In contrast, NADi-351 showed no goblet cell metaplasia and intact crypts, comparable to the control group (DMSO). See FIG. 7.

Further guidance of using the inhibitors disclosed herein for inhibiting the NTC can be found in the Examples section, below.

Pharmaceutical Formulations

Also provided herein are pharmaceutical formulations that include the compounds of the disclosure, and one or more pharmaceutically acceptable excipients. As used herein, the term "excipient" refers to any pharmaceutically acceptable additive, carrier, diluent, adjuvant, or other ingredient, other than the active pharmaceutical ingredient (API). The term "pharmaceutically acceptable carrier" refers to a medium that does not interfere with the effectiveness of the biological activity of the active ingredient(s) and is not toxic to the host to which it is administered.

The compounds disclosed herein can be as a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The compound or salts of the disclosure can be administered to a subject or patient in a therapeutically effective amount. The compound or salts can be administered alone or as part of a pharmaceutically acceptable composition or formulation. In addition, the compounds or salts can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds or salts disclosed herein can be administered in combination with one or more additional pharmaceutically active compounds/agents. The additional pharmaceutically active compounds/agents may be traditional small organic chemical molecules or can be macromolecules such as a proteins, antibodies, peptibodies, DNA, RNA or fragments of such macromolecules.

The compounds or salts disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

When a subject or patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

Example #1—NADi-260: (Z)-2-(5-(4-((1H-1,2,4-triazol-3-yl)methoxy)-3-fluoro-5-methoxybenzylidene)-4-oxo-2-thioxothiazolidin-3-yl)-N,N-dimethylacetamide

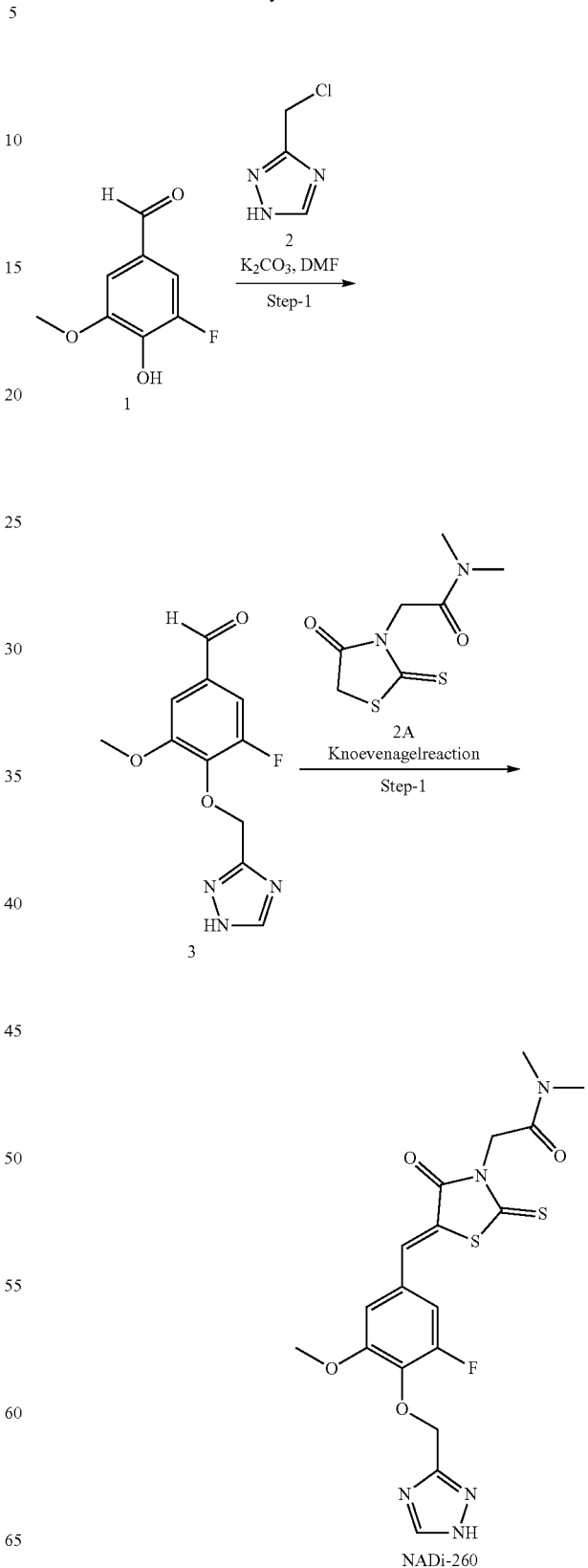

-continued

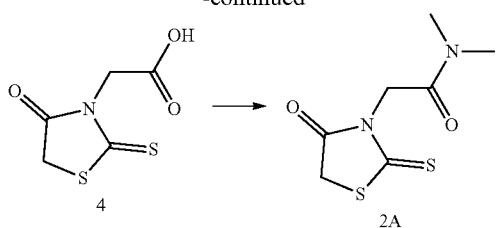

4-((1H-1,2,4-triazol-3-yl)methoxy)-3-fluoro-5-methoxybenzaldehyde (3): To a stirred solution of 3-fluoro-4-hydroxy-5-methoxybenzaldehyde (1, 10 g, 58.82 mmol) in ACN (300 mL), K$_2$CO$_3$ (16.25 g, 117.64 mmol), 3-(chloromethyl)-1H-1,2,4-triazole (8.96 g, 58.82 mmol) in DMF (10 mL) and TEA (8.26 mL, 58.82 mmol) was added at rt and the reaction mixture was stirred at 90° C. for 3 h. The progress of the reaction was monitored by TLC. After completion of reaction, the reaction mixture was diluted with ethyl acetate and the organic layer was washed with water and brine. Combined organic layer was dried over anhydrous Na$_2$SO$_4$ and concentrated under reduced pressure. The crude compound was purified by silica gel column chromatography (40-60% EtOAc/hexane) to afford compound 3 (6 g, 40.65%) as white solid. $^1$H NMR (400 MHz, DMSO-d6): δ 14.00 (s, 1H), 9.88 (s, 1H), 7.44-7.39 (m, 2H), 5.20 (s, 2H), 3.91 (s, 3H), 1H (exchangeable) merged in solvent peak; LC-MS: m/z 252.0 [M+H]$^+$.

To a stirred solution of 4-((1H-1,2,4-triazol-3-yl)methoxy)-3-fluoro-5-methoxybenzaldehyde (500 mg, 1.99 mmol) in Acetic acid (10 mL), N,N-dimethyl-2-(4-oxo-2-thioxothiazolidin-3-yl)acetamide (500 mg, 1.99 mmol), ammonium acetate (782 mg, 10 mmol) was added. The reaction mixture was stirred at 120° C. for 4 h. The progress of the reaction was monitored by TLC. After completion of reaction, the reaction mixture was diluted with ethyl acetate and the organic layer was washed with water and brine. Combined organic layer was dried over anhydrous Na$_2$SO$_4$ and concentrated under reduced pressure. The crude compound was purified by silica gel column chromatography (0-5% MeOH/DCM) to afford NADi-260 (320 mg, 35.63%) as white solid. $^1$H NMR (400 MHz, DMSO-d6): δ 14.01 (s, 1H), 8.54 (s, 1H), 7.81 (s, 1H), 7.20-7.14 (m, 2H), 5.17 (s, 2H), 4.94 (s, 2H), 3.91 (s, 3H), 3.09 (s, 3H), 2.85 (s, 3H); LC-MS: m/z 452.05 [M+H]$^+$; HPLC: 99.86%.

N,N-dimethyl-2-(4-oxo-2-thioxothiazolidin-3-yl)acetamide (2A): To a stirred solution of 2-(4-oxo-2-thioxothiazolidin-3-yl)acetic acid (5 g, 26.15 mmol) in DMF (50 mL), HATU (14.89 g, 39.21 mmol), N,N dimethylamine hydrochloride (4.26 g, 52.30 mmol) was added. The reaction mixture was stirred at rt for 5 h. The progress of the reaction was monitored by TLC. After completion of reaction add ice cold water and extracted with EtOAc. Combined organic layer was washed with brine, dried over anhydrous Na$_2$SO$_4$ and concentrated under reduced pressure. The crude compound was purified by column chromatography to afford N,N-dimethyl-2-(4-oxo-2-thioxothiazolidin-3-yl)acetamide (3.5 g, 61.41%) as a yellow solid. $^1$H NMR (400 MHz, DMSO-d6): δ 4.74 (s, 2H), 4.39 (s, 2H), 3.06 (s, 3H), 2.82 (s, 3H); LC-MS: m/z 218.85 [M+H]$^+$.

Example #2—NADi-327: (Z)-2-(5-(4-((1H-1,2,4-triazol-3-yl)methoxy)-3-fluoro-5-methoxybenzylidene)-4-oxo-2-thioxothiazolidin-3-yl)-N-(4-chlorophenyl)-N-methylacetamide

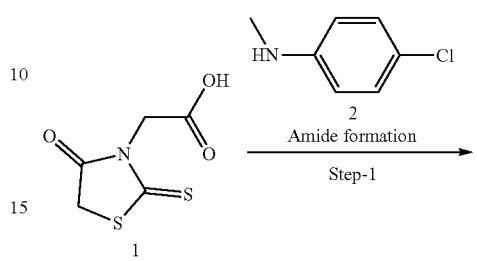

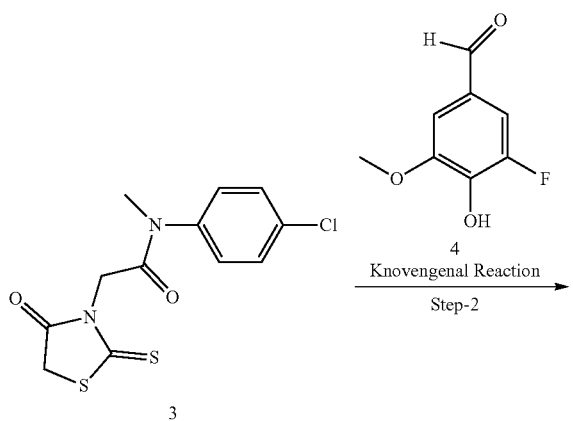

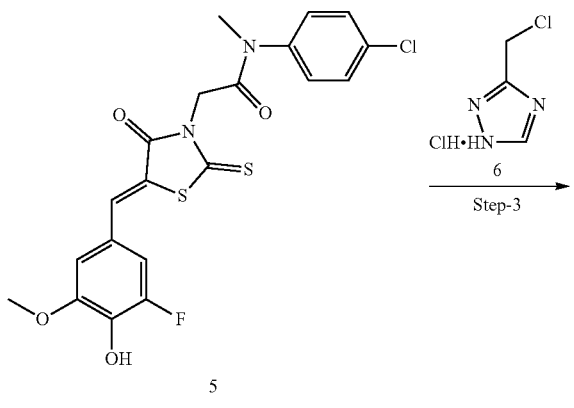

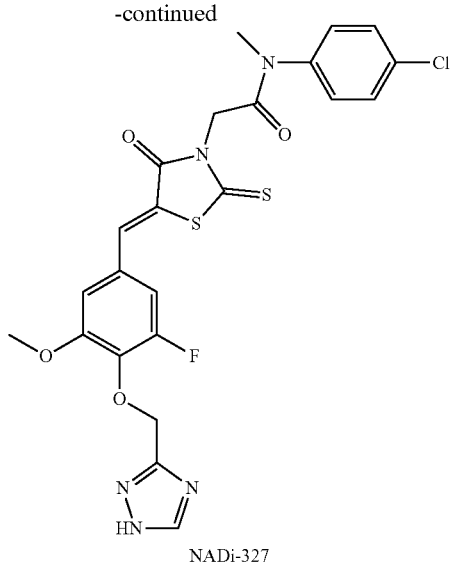

NADi-327

N-(4-chlorophenyl)-N-methyl-2-(4-oxo-2-thioxothiazolidin-3-yl)acetamide (3): To a stirred solution of 2-(4-oxo-2-thioxothiazolidin-3-yl)acetic acid (1 g, 5.22 mmol) in DCM (50 mL), was added oxalyl chloride (990 mg, 7.80 mmol) and DMF (0.5 mL) (Catalytical) at 0° C. The reaction mixture was stirred at rt for 30 min. then reaction mixture was concentrated and was dissolved in DCM (50 mL), to this 4-chloro-N-methylaniline (739 mg, 5.22 mmol) and DIPEA (1.87 mL, 10.45 mmol) were added at 0° C. The reaction mixture was stirred at rt for 1 h. The progress of the reaction was monitored by TLC. After completion of reaction, reaction mixture was diluted with DCM and wash with water. Combined organic layer was washed with brine, dried over anhydrous $Na_2SO_4$ and concentrated under reduced pressure. The crude compound was purified by column chromatography (50% EA:Hexane) to afford N-(4-chlorophenyl)-N-methyl-2-(4-oxo-2-thioxothiazolidin-3-yl)acetamide (300 mg, 19%) as a yellow solid. $^1$H NMR (400 MHz, DMSO-d6): δ 7.56 (d, J=18.0 Hz, 4H), 4.36 (d, J=20.8 Hz, 3H), 3.15 (s, 2H), 2H merged in solvent peak; LC-MS: m/z 315.0 $[M+H]^+$.

(Z)—N-(4-chlorophenyl)-2-(5-(3-fluoro-4-hydroxy-5-methoxybenzylidene)-4-oxo-2-thioxothiazolidin-3-yl)-N-methylacetamide (5): To a stirred solution of N-(4-chlorophenyl)-N-methyl-2-(4-oxo-2-thioxothiazolidin-3-yl)acetamide (3, 300 mg, 0.95 mmol) and 3-fluoro-4-hydroxy-5-methoxybenzaldehyde (162 mg, 0.95 mmol) in acetic acid (30 mL), sodium acetate (391 mg, 4.77 mmol) was added at rt. The reaction mixture was stirred at 90° C. for 16 h. The progress of the reaction was monitored by TLC. After completion of reaction, the reaction mixture was cooled and added to ice cold water. The solid precipitated was filtered off and wash with water and dried to afford #5 as a light yellow solid which is used for next step without purification. $^1$H NMR (400 MHz, DMSO-d6): δ 10.42 (brs, 1H), 7.77 (s, 1H), 7.62-7.56 (m, 4H), 7.16 (d, J=11.6 Hz, 1H), 7.08 (s, 1H), 4.50 (s, 2H), 3.89 (s, 3H), 3.18 (s, 3H); LC-MS: m/z 467.05 $[M+H]^+$.

To a stirred solution of (Z)—N-(4-chlorophenyl)-2-(5-(3-fluoro-4-hydroxy-5-methoxybenzylidene)-4-oxo-2-thioxothiazolidin-3-yl)-N-methylacetamide (300 mg, 0.64 mmol) and 3-(chloromethyl)-1H-1,2,4-triazole hydrochloride (98 mg, 0.64 mmol) in DMF (5 mL), potassium carbonate (177 mg, 1.28 mmol) and TEA (65 mg, 0.64 mmol) were added. The reaction mixture was stirred at 80° C. for 3 h. The progress of the reaction was monitored by TLC. After completion of reaction, the reaction mixture was cooled and quenched with ice cold water and extracted with EtOAc. Combined organic layer was washed with brine, dried over anhydrous $Na_2SO_4$ and concentrated under reduced pressure. The crude compound was purified by column chromatography to afford NADi-327 (90 mg, 25.56%) as a light yellow solid. $^1$H NMR (400 MHz, DMSO-d6): δ 14.00 (brs, 1H), 8.51 (brs, 1H), 7.81 (s, 1H), 7.64-7.56 (m, 4H), 7.18-7.13 (m, 2H), 5.18 (s, 2H), 4.51 (s, 2H), 3.91 (s, 3H), 3.18 (s, 3H); LC-MS: m/z 548.05 $[M+H]^+$; HPLC: 98.34%.

Example #3—NADi-333: (Z)-2-(5-(4-((1H-1,2,4-triazol-3-yl)methoxy)-3-fluoro-5-methoxybenzylidene)-4-oxo-2-thioxothiazolidin-3-yl)-N-(4-chlorophenyl)acetamide

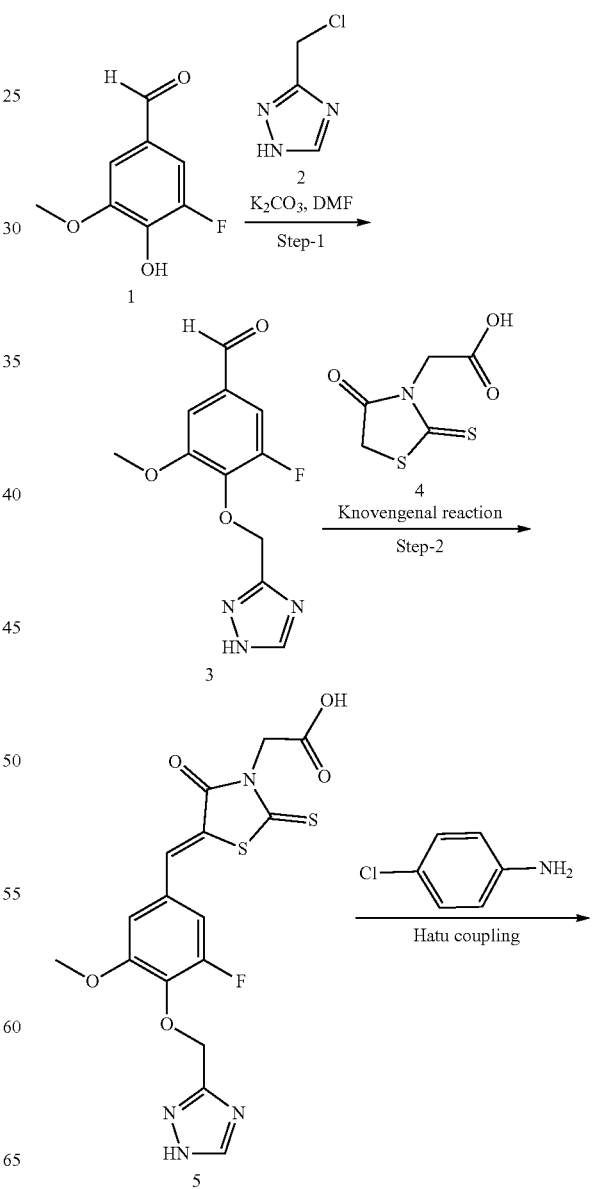

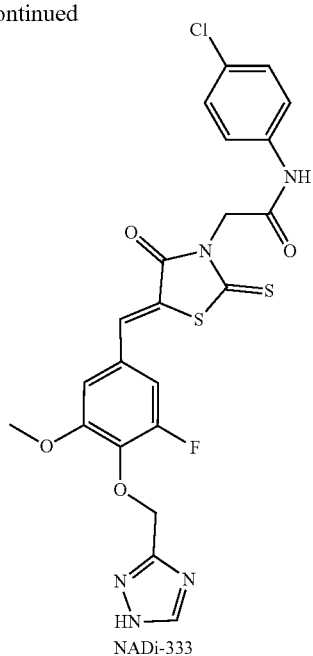

NADi-333

4-((1H-1,2,4-triazol-3-yl)methoxy)-3-fluoro-5-methoxybenzaldehyde (3): To a stirred solution of 3-fluoro-4-hydroxy-5-methoxybenzaldehyde (1, 10 g, 58.82 mmol) in ACN (300 mL), $K_2CO_3$ (16.25 g, 117.64 mmol), 3-(chloromethyl)-1H-1,2,4-triazole (8.96 g, 58.82 mmol) in DMF (10 mL) and TEA (8.26 mL, 58.82 mmol) was added at rt and the reaction mixture was stirred at 90° C. for 3 h. The progress of the reaction was monitored by TLC. After completion of reaction, the reaction mixture was diluted with ethyl acetate and the organic layer was washed with water and brine. Combined organic layer was dried over anhydrous $Na_2SO_4$ and concentrated under reduced pressure. The crude compound was purified by silica gel column chromatography (40-60% EtOAc/hexane) to afford compound 3 (6 g, 40.65%) as white solid. $^1$H NMR (400 MHz, DMSO-d6): δ 14.00 (s, 1H), 9.88 (s, 1H), 7.44-7.39 (m, 2H), 5.20 (s, 2H), 3.91 (s, 3H), 1H (exchangeable) merged in solvent peak; LC-MS: m/z 252.0 [M+H]$^+$.

(Z)-2-(5-(4-((1H-1,2,4-triazol-3-yl)methoxy)-3-fluoro-5-methoxybenzylidene)-4-oxo-2-thioxothiazolidin-3-yl)acetic acid (5): To a stirred solution of 4-((1H-1,2,4-triazol-3-yl)methoxy)-3-fluoro-5-methoxybenzaldehyde (450 mg, 1.79 mmol) in acetic acid (20 mL), 2-(4-oxo-2-thioxothiazolidin-3-yl)acetic acid (411 mg, 2.14 mmol) and sodium acetate (735 mg, 8.95 mmol) were added. The reaction mixture was stirred at 90° C. for 16 h. The progress of the reaction was monitored by TLC. After completion of reaction, the reaction mixture cooled and quenched with ice cold water. The solid material was filtered and wash with water and dried to afford #5 as a off white solid. (450 mg, 57%). $^1$H NMR (400 MHz, DMSO-d6): δ 14.00 (s, 1H), 13.50 (brs, 1H), 8.52 (s, 1H), 7.85 (s, 1H), 7.19-7.14 (m, 2H), 5.17 (s, 2H), 4.75 (s, 2H), 3.91 (s, 3H); LC-MS: m/z 425.0 [M+H]$^+$.

To a stirred solution of (Z)-2-(5-(4-((1H-1,2,4-triazol-3-yl)methoxy)-3-fluoro-5-methoxybenzylidene)-4-oxo-2-thioxothiazolidin-3-yl)acetic acid (100 mg, 0.23 mmol) in DMF (5 mL), HATU (133 mg, 0.35 mmol), 4-chloroaniline (59 mg, 0.46 mmol) and DIPEA (59 mg, 0.46 mmol) were added. The reaction mixture was stirred at rt for 16 h. The progress of the reaction was monitored by TLC. After completion of reaction, ice cold water was added and extracted with EtOAc. Combined organic layer was washed with brine, dried over anhydrous $Na_2SO_4$ and concentrated under reduced pressure. The crude compound was purified by column chromatography to afford NADi-333 (40 mg, 32%) as a light yellow solid. $^1$H NMR (400 MHz, DMSO-d6, VT at 80° C.): δ 13.95 (brs, 1H), 10.34 (s, 1H), 8.42 (brs, 1H), 7.81 (s, 1H), 7.56 (d, J=7.6 Hz, 2H), 7.36 (d, J=6.8 Hz, 2H), 7.17-7.12 (m, 2H), 5.22 (s, 2H), 4.91 (s, 2H), 3.92 (s, 3H); LC-MS: m/z 534.10 [M+H]$^+$; HPLC: 96.65%.

Example #4—NADi-335: (Z)-2-(4-(4-((4H-1,2,4-triazol-3-yl)methoxy)-3-fluoro-5-methoxybenzylidene)-3-methyl-5-oxo-2-thioxoimidazolidin-1-yl)-N,N-dimethylacetamide

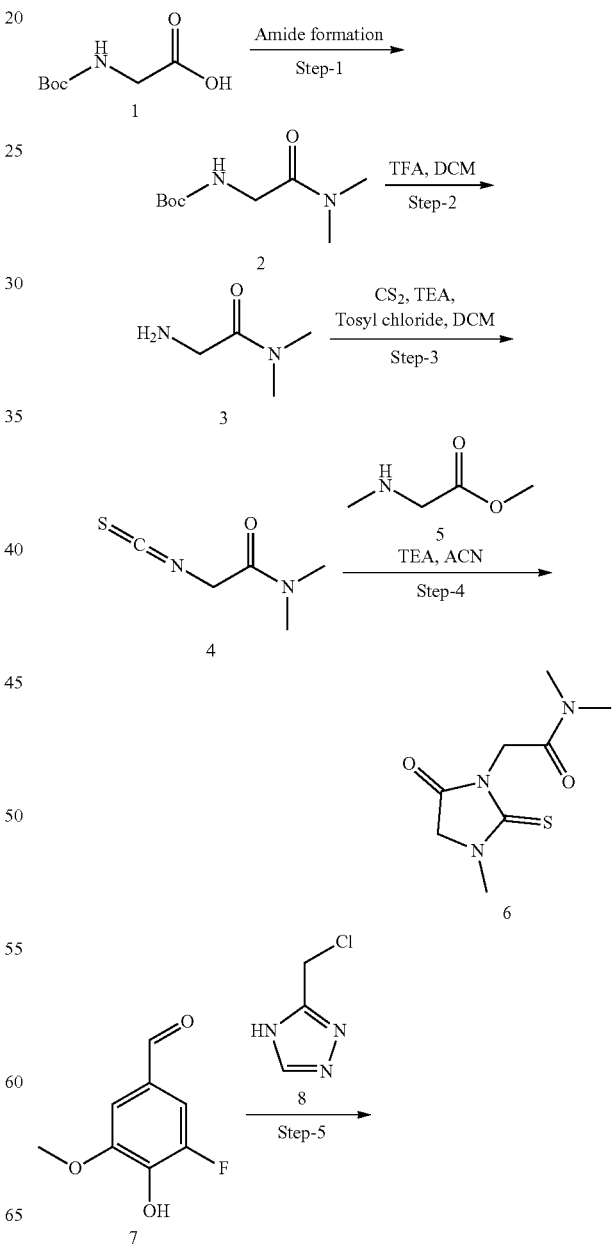

-continued

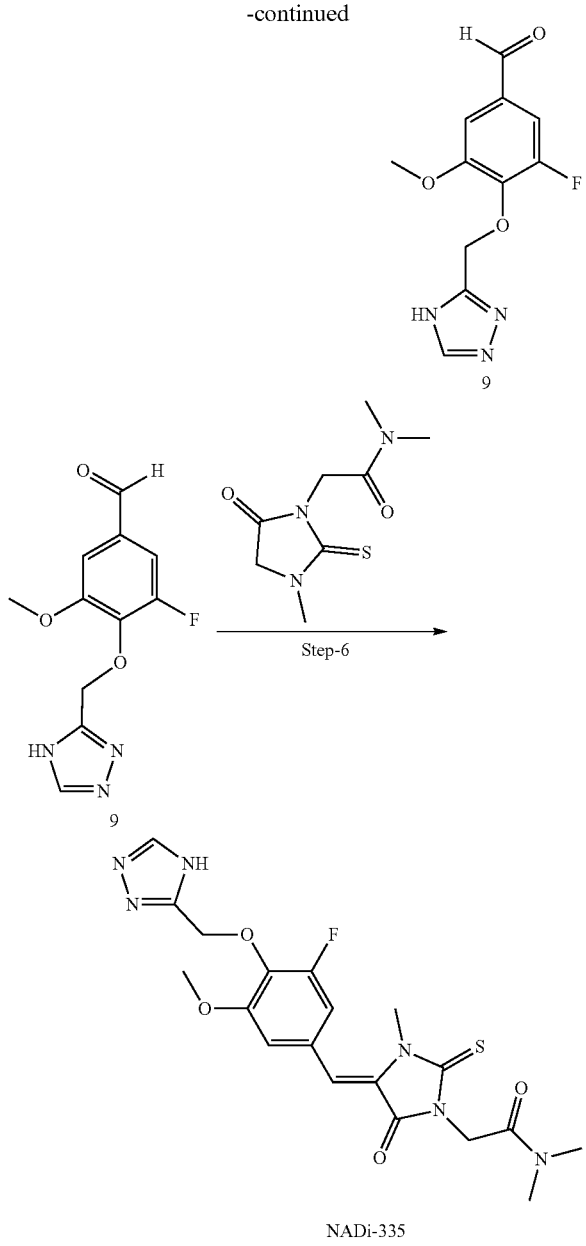

tert-Butyl (2-(dimethylamino)-2-oxoethyl)carbamate (2): To a stirred solution of (tert-butoxycarbonyl)glycine (2 g, 11.41 mmol) in DCM (50 mL), EDCl·HCl (3.27 g, 17.14 mmol), HOBT (1.54 g, 11.41 mmol), DMAP (1.36 g, 11.17 mmol) and dimethyl amine hydrochloride (1.03 g, 12.57 mmol) were added at rt. The reaction mixture was stirred at rt for 16 h. The progress of the reaction was monitored by TLC. After completion of reaction, reaction mixture was diluted with DCM and wash with water. Combined organic layer was washed with brine, dried over anhydrous $Na_2SO_4$ and concentrated under reduced pressure. The crude compound was purified by column chromatography (5% MeOH:DCM) to afford tert-butyl (2-(dimethylamino)-2-oxoethyl) carbamate (2.0 g, 86%) as an off white solid. $^1$H NMR (400 MHz, DMSO-d6): δ 6.65 (s, 1H), 3.74 (d, J=3.6 Hz, 2H), 2.92 (s, 3H), 2.82 (s, 3H), 1.38 (s, 9H).

2-Amino-N,N-dimethylacetamide (3): To a stirred solution of tert-butyl (2-(dimethylamino)-2-oxoethyl)carbamate (2, 2 g, 9.88 mmol) in DCM (30 mL), TFA (10 mL) was added at 0° C. The reaction mixture was stirred at rt for 1 h. The progress of the reaction was monitored by TLC. After completion of reaction, all volatile was concentrated on rotary evaporator and triturate with diethyl ether and dried to afford 2-amino-N,N-dimethylacetamide TFA salt as a light yellow solid. Used as such for next step without further purification. $^1$H NMR (400 MHz, DMSO-d6): δ 8.07 (brs, 2H), 3.83 (s, 2H), 2.93 (s, 3H), 2.89 (s, 3H).

2-Isothiocyanato-N,N-dimethylacetamide (4): To a stirred solution of 2-amino-N,N-dimethylacetamide (TFA salt) (500 mg, 2.52 mmol) in DCM (50 mL), carbon disulfide (383 mg, 5.04 mmol) and TEA (1.42 mL, 10.10 mmol) were added at 0° c. The reaction mixture was stirred for 30 min, then added tosyl chloride (479 mg, 2.52 mmol) at rt. The reaction mixture was further stirred for 4 h. The progress of the reaction was monitored by TLC. After completion of reaction, diluted with DCM and wash with citric acid solution. Combined organic layer was washed with brine, dried over anhydrous $Na_2SO_4$ and concentrated under reduced pressure to afford 2-isothiocyanato-N,N-dimethylacetamide (500 mg, 70%) as an off white solid which was used for next step without further purification.

N,N-dimethyl-2-(3-methyl-5-oxo-2-thioxoimidazolidin-1-yl)acetamide (6): To a stirred solution of 2-isothiocyanato-N,N-dimethylacetamide (500 mg, 3.46 mmol) in ACN (25 mL), methyl methylglycinate (HCl Salt) (482 mg, 3.46 mmol) and TEA (351 mg, 3.46 mmol) were added at rt. The reaction mixture was stirred at rt for 2 h. The progress of the reaction was monitored by TLC. After completion of reaction, diluted with EA and wash with water. Combined organic layer was washed with brine, dried over anhydrous $Na_2SO_4$ and concentrated under reduced pressure. The crude compound was purified by column chromatography (5% MeOH:DCM) to afford N,N-dimethyl-2-(3-methyl-5-oxo-2-thioxoimidazolidin-1-yl)acetamide (150 mg, 20%) as an off white solid. $^1$H NMR (400 MHz, DMSO-d6): δ 4.53 (s, 2H), 4.36 (s, 2H), 3.23 (s, 3H), 3.03 (s, 3H), 2.82 (s, 3H).

4-((4H-1,2,4-triazol-3-yl)methoxy)-3-fluoro-5-methoxybenzaldehyde (9): To a stirred solution of 3-fluoro-4-hydroxy-5-methoxybenzaldehyde (7, 1 g, 5.88 mmol) in ACN (25 mL), potassium carbonate (2.02 g 14.70 mmol), 3-(chloromethyl)-4H-1,2,4-triazole (688 mg, 5.88 mmol) and TEA (1.24 mL, 8.82 mmol) were added at rt. The reaction mixture was stirred at 70° C. for 2 h. The progress of the reaction was monitored by TLC. After completion of reaction, the reaction mixture was filtered through Buchner funnel. Concentrated organic layer under reduced pressure. The crude compound was purified by column chromatography (5% MeOH:DCM) to afford 4-((4H-1,2,4-triazol-3-yl)methoxy)-3-fluoro-5-methoxybenzaldehyde (550 mg, 37.41%) as an off white solid. $^1$H NMR (400 MHz, DMSO-d6): δ 14.09 (brs, 1H), 9.98 (brs, 1H), 9.88 (s, 1H), 7.44-7.35 (m, 2H), 5.21 (s, 2H), 3.91 (s, 3H).

To a stirred solution of N,N-dimethyl-2-(3-methyl-5-oxo-2-thioxoimidazolidin-1-yl)acetamide (6, 200 mg, 0.93 mmol) and 4-((4H-1,2,4-triazol-3-yl)methoxy)-3-fluoro-5-methoxybenzaldehyde (233 mg, 0.93 mmol) in acetic acid (15 mL), sodium acetate (381 mg, 4.65 mmol) were added at rt. The reaction mixture was stirred at 90° C. for 16 h. The progress of the reaction was monitored by TLC. After completion of reaction, the reaction mixture was cooled and added to an ice cold water. The solid precipitated was filtered and wash with water. The crude compound was purified by column chromatography to afford NADi-335 (40 mg, 11.23%) as a light yellow solid. $^1$H NMR (400 MHz, DMSO-d6): δ 13.98 (brs, 1H), 8.52 (s, 1H), 7.85 (s, 1H), 7.75 (d, J=12.4 Hz, 1H), 6.93 (s, 1H), 5.12 (s, 2H), 4.73 (s, 2H), 3.86 (s, 3H), 3.59 (s, 3H), 3.07 (s, 3H), 2.83 (s, 3H); LC-MS: m/z 449.10 [M+H]+; HPLC: 95.29%.

Example #5—NADi-351: (Z)-2-(5-(1-(4-((1H-1,2,4-triazol-3-yl)methoxy)-3-fluoro-5-methoxyphenyl)ethylidene)-4-oxo-2-thioxothiazolidin-3-yl)-N,N-dimethylacetamide

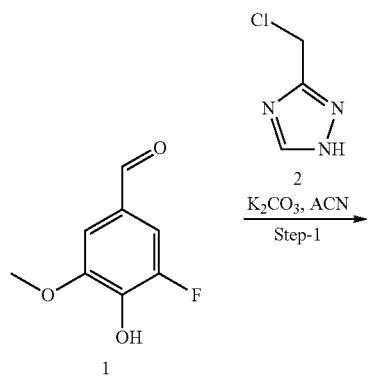

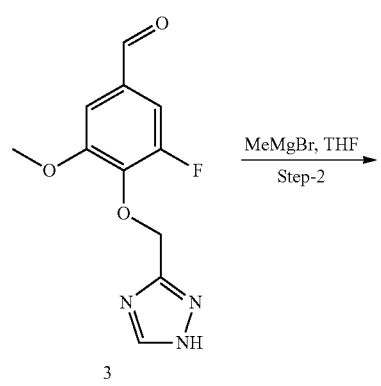

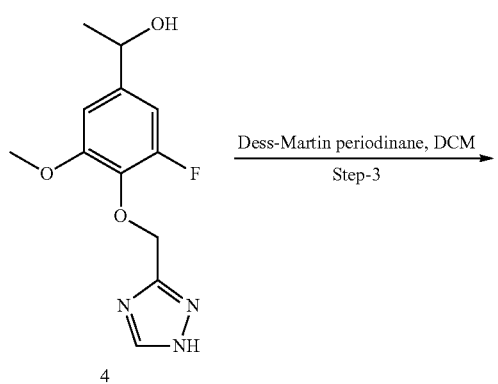

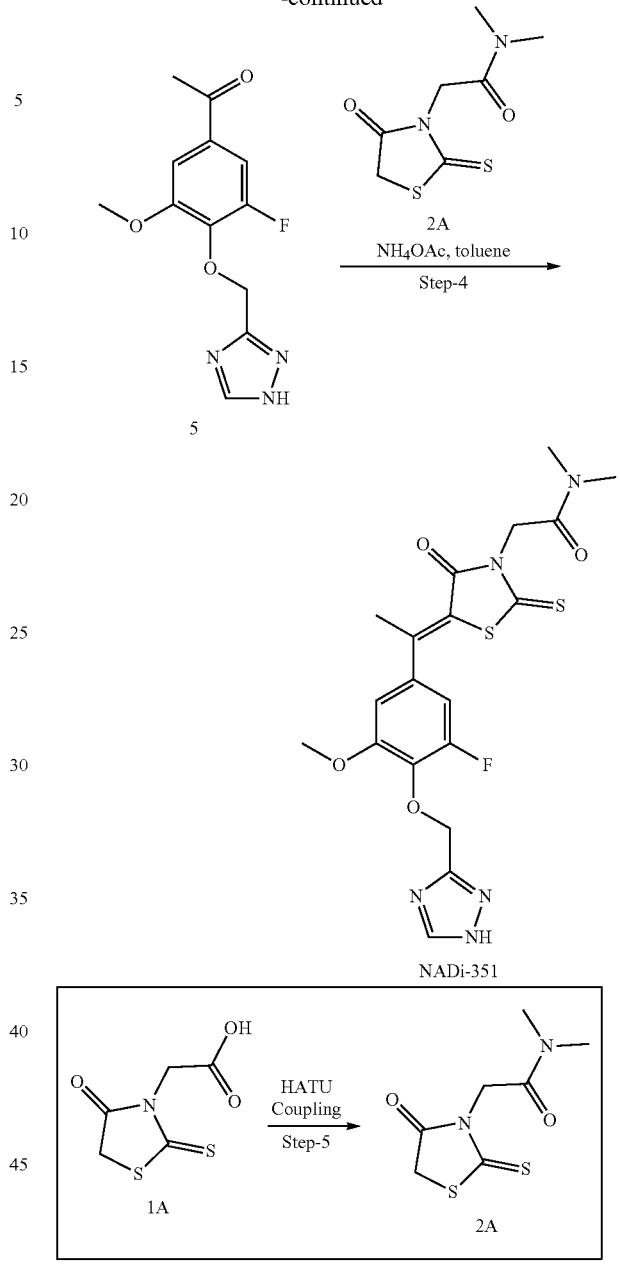

4-((1H-1,2,4-triazol-3-yl)methoxy)-3-fluoro-5-methoxybenzaldehyde (3): To a stirred solution of 3-fluoro-4-hydroxy-5-methoxybenzaldehyde (1, 10 g, 58.82 mmol) in ACN (300 mL), K₂CO₃ (16.25 g, 117.64 mmol), 3-(chloromethyl)-1H-1,2,4-triazole (2, 8.96 g, 58.82 mmol) in DMF (10 mL) and TEA (8.26 mL, 58.82 mmol) were added at rt and the reaction mixture was stirred at 90° C. for 3 h. The progress of the reaction was monitored by TLC. After completion of reaction, the reaction mixture was diluted with ethyl acetate and the organic layer was washed with water and brine. Combined organic layer was dried over anhydrous Na₂SO₄ and concentrated under reduced pressure. The crude compound was purified by silica gel column chromatography (40-60% EtOAc/hexane) to afford compound 3 (6 g, 40.65%) as white solid. ¹H NMR (400 MHz, DMSO-d6): b 14.00 (s, 1H), 9.88 (s, 1H), 7.44-7.39 (m, 2H), 5.20 (s, 2H), 3.91 (s, 3H), 1H (exchangeable) merged in solvent peak; LC-MS: m/z 252.0 [M+H]+.

1-(4-(((1H-1,2,4-triazol-3-yl)methoxy)-3-fluoro-5-methoxyphenyl)ethan-1-ol (4): To a stirred solution of 3-fluoro-4-hydroxy-5-methoxybenzaldehyde (3, 3 g, 11.94 mmol) in dry THF (30 mL) at 0° C., methyl magnesium bromide (11.94 mL, 35.82 mmol) was added drop wise and the reaction mixture was stirred at 0° C. for 2 h. The progress of the reaction was monitored by TLC. After completion of reaction, the reaction mixture was quenched with saturated NH$_4$Cl solution. The aqueous layer was extracted with EtOAc. Combined organic layer was washed with water, dried over anhydrous Na$_2$SO$_4$ and concentrated under reduced pressure. The crude compound was purified by Combiflash column chromatography (1-5% MeOH/DCM) to afford compound 4 (2.2 g, 68.96%) as an oily liquid. LC-MS: m/z 268.00 [M+H]$^+$.

1-(4-(((1H-1,2,4-triazol-3-yl)methoxy)-3-fluoro-5-methoxyphenyl)ethan-1-one (5): To a stirred solution of 1-(4-(((1H-1,2,4-triazol-3-yl)methoxy)-3-fluoro-5-methoxyphenyl)ethan-1-ol (4, 1.1 g, 4.11 mmol) in DCM (50 mL), Dess martin periodinane (3.48 g, 8.22 mmol) was added at rt and the reaction mixture was stirred at the same temperature for 1 h. The progress of the reaction was monitored by TLC. After completion of reaction, the reaction mixture was added water. The aqueous layer was extracted with EtOAc. Combined organic layer was washed with water, dried over anhydrous Na$_2$SO$_4$ and concentrated under reduced pressure. The crude compound was purified by Combiflash column chromatography (0.5-3% MeOH/DCM) to afford compound 5 (1 g, 91.65%) as white solid. $^1$H NMR (400 MHz, DMSO-d6): δ 13.99 (s, 1H), 8.52 (s, 1H), 7.45-7.39 (m, 2H), 5.15 (s, 2H), 3.89 (s, 3H), 2.56 (s, 3H); LC-MS: m/z 266.05 [M+H]$^+$.

To a stirred solution of 1-(4-(((1H-1,2,4-triazol-3-yl)methoxy)-3-fluoro-5-methoxyphenyl)ethan-1-one (700 mg, 2.63 mmol) in Toluene (30 mL), N,N-dimethyl-2-(4-oxo-2-thioxothiazolidin-3-yl)acetamide (576 mg, 2.63 mmol), ammonium acetate (1 g, 13.19 mmol) were added. The reaction mixture was stirred at 120° C. for 4 h. The progress of the reaction was monitored by TLC. After completion of reaction, the reaction mixture cooled and quenched with ice cold water and extracted with EtOAc. Combined organic layer was washed with brine, dried over anhydrous Na$_2$SO$_4$ and concentrated under reduced pressure. The crude compound was purified by preparative HPLC to afford NADi-351 (90 mg, 7.5%). $^1$H NMR (400 MHz, DMSO-d6): δ 14.01 (s, 1H), 8.54 (s, 1H), 7.05-6.98 (m, 2H), 5.10 (s, 2H), 4.88 (s, 2H), 3.87 (s, 3H), 3.09 (s, 3H), 2.84 (s, 3H), 2.70 (s, 3H); LC-MS: m/z 466.35 [M+H]$^+$; HPLC: 96.78%.

N,N-dimethyl-2-(4-oxo-2-thioxothiazolidin-3-yl)acetamide (2A): To a stirred solution of 2-(4-oxo-2-thioxothiazolidin-3-yl)acetic acid (1A, 5 g, 26.15 mmol) in DMF (50 mL), HATU (14.89 g, 39.21 mmol), N,N dimethylamine hydrochloride (4.26 g, 52.30 mmol) were added. The reaction mixture was stirred at rt for 5 h. The progress of the reaction was monitored by TLC. After completion of reaction, ice cold water was added to it and extracted aqueous layer with EtOAc. Combined organic layer was washed with brine, dried over anhydrous Na$_2$SO$_4$ and concentrated under reduced pressure. The crude compound was purified by column chromatography to afford N,N-dimethyl-2-(4-oxo-2-thioxothiazolidin-3-yl)acetamide (2A, 4 g, 70.17%) as a yellow solid. $^1$H NMR (400 MHz, DMSO-d6): δ 4.74 (s, 2H), 4.39 (s, 2H), 3.06 (s, 3H), 2.82 (s, 3H); LC-MS: m/z 218.85 [M+H]$^+$.

Example #6—NADi-355: (Z)-2-(5-(1-(4-(((1H-1,2,4-triazol-3-yl)methoxy)-3-fluoro-5-methoxyphenyl)ethylidene)-4-oxo-2-thioxothiazolidin-3-yl)-N-(4-chlorophenyl)-N-methylacetamide

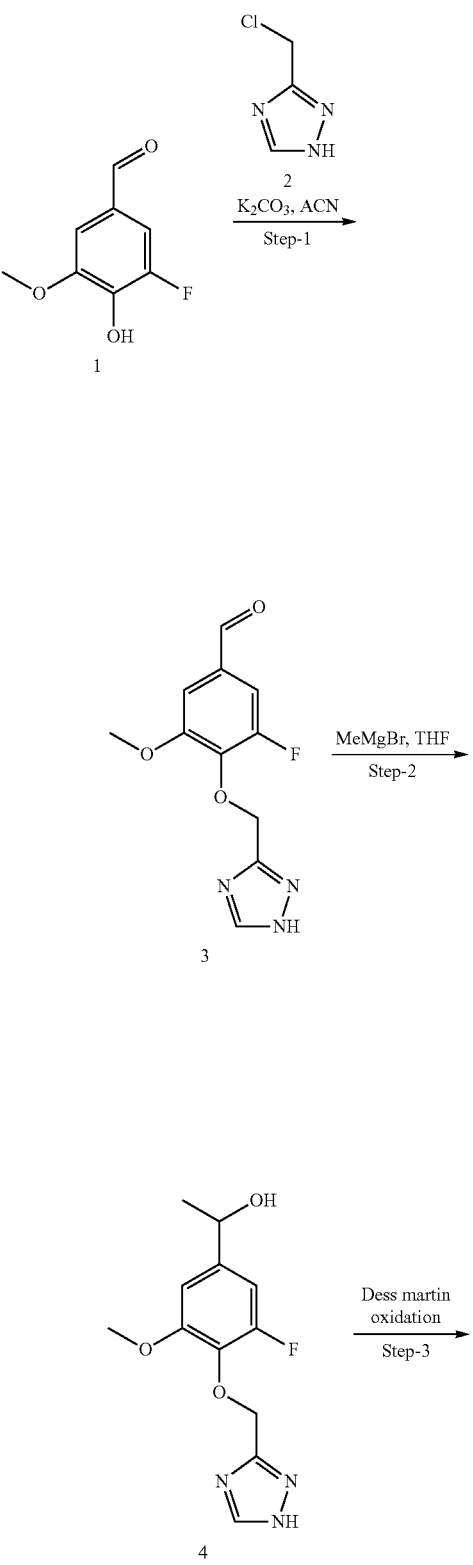

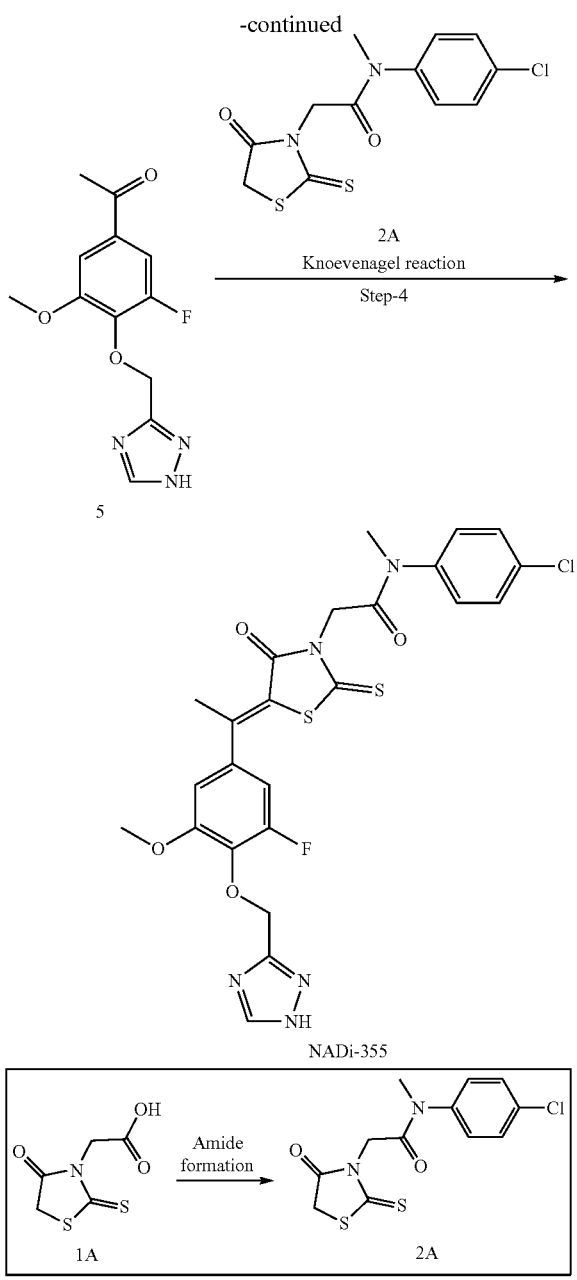

4-((1H-1,2,4-triazol-3-yl)methoxy)-3-fluoro-5-methoxybenzaldehyde (3): To a stirred solution of 3-fluoro-4-hydroxy-5-methoxybenzaldehyde (1, 10 g, 58.82 mmol) in ACN (300 mL), K$_2$CO$_3$ (16.25 g, 117.64 mmol), 3-(chloromethyl)-1H-1,2,4-triazole (8.96 g, 58.82 mmol) in DMF (10 mL) and TEA (8.26 mL, 58.82 mmol) were added at rt and the reaction mixture was stirred at 90° C. for 3 h. The progress of the reaction was monitored by TLC. After completion of reaction, the reaction mixture was diluted with ethyl acetate and the organic layer was washed with water and brine. Combined organic layer was dried over anhydrous Na$_2$SO$_4$ and concentrated under reduced pressure. The crude compound was purified by silica gel column chromatography (40-60% EtOAc/hexane) to afford compound 3 (6 g, 40.65%) as white solid. $^1$H NMR (400 MHz, DMSO-d6): δ 14.00 (s, 1H), 9.88 (s, 1H), 7.44-7.39 (m, 2H), 5.20 (s, 2H), 3.91 (s, 3H), 1H (exchangeable) merged in solvent peak; LC-MS: m/z 252.0 [M+H]$^+$.

1-(4-((1H-1,2,4-triazol-3-yl)methoxy)-3-fluoro-5-methoxyphenyl)ethan-1-ol (4): To a stirred solution of 3-fluoro-4-hydroxy-5-methoxybenzaldehyde (3, 3 g, 11.94 mmol) in dry THF (30 mL) at 0° C., methyl magnesium bromide (11.94 mL, 35.82 mmol) was added drop wise and the reaction mixture was stirred at the 0° C. for 2 h. The progress of the reaction was monitored by TLC. After completion of reaction, the reaction mixture was quenched with saturated NH$_4$Cl solution. The aqueous layer was extracted with EtOAc. Combined organic layer was washed with water, dried over anhydrous Na$_2$SO$_4$ and concentrated under reduced pressure. The crude compound was purified by Combiflash column chromatography (1-5% MeOH/DCM) to afford compound 4 (2.2 g, 68.96%) as an oily liquid. LC-MS: m/z 268.00 [M+H]$^+$.

1-(4-((1H-1,2,4-triazol-3-yl)methoxy)-3-fluoro-5-methoxyphenyl)ethan-1-one (5): To a stirred solution of 1-(4-((1H-1,2,4-triazol-3-yl)methoxy)-3-fluoro-5-methoxyphenyl)ethan-1-ol (4, 1.1 g, 4.11 mmol) in DCM (50 mL), Dess martin periodinane (3.48 g, 8.22 mmol) was added at rt and the reaction mixture was stirred at the same temperature for 1 h. The progress of the reaction was monitored by TLC. After completion of reaction, the reaction mixture was added water. The aqueous layer was extracted with EtOAc. Combined organic layer was washed with water, dried over anhydrous Na$_2$SO$_4$ and concentrated under reduced pressure. The crude compound was purified by Combiflash column chromatography (0.5-3% MeOH/DCM) to afford compound 5 (1 g, 91.65%) as white solid. $^1$H NMR (400 MHz, DMSO-d6): δ 13.99 (s, 1H), 8.52 (s, 1H), 7.45-7.39 (m, 2H), 5.15 (s, 2H), 3.89 (s, 3H), 2.56 (s, 3H); LC-MS: m/z 266.05 [M+H]$^+$.

To a stirred solution of N-(4-chlorophenyl)-N-methyl-2-(4-oxo-2-thioxothiazolidin-3-yl)acetamide (200 mg, 0.63 mmol) in Toluene (20 mL), 1-(4-((1H-1,2,4-triazol-3-yl)methoxy)-3-fluoro-5-methoxyphenyl)ethan-1-one (168 mg, 0.63 mmol), ammonium acetate (229 mg, 3.17 mmol) were added. The reaction mixture was stirred at 120° C. for 4 h. The progress of the reaction was monitored by TLC. After completion of reaction, the reaction mixture cooled and quenched with ice cold water and extracted with EtOAc. Combined organic layer was washed with brine, dried over anhydrous Na$_2$SO$_4$ and concentrated under reduced pressure. The crude compound was purified by preparative HPLC to afford NADi-355 as a light yellow solid (19 mg, 5.32%). $^1$H NMR (400 MHz, DMSO-d6, VT at 80° C.): δ 13.80 (brs, 1H), 8.46 (s, 1H), 7.57-7.48 (m, 4H), 6.99 (s, 2H), 5.15 (s, 2H), 4.59 (s, 2H), 3.87 (s, 3H), 3.23 (s, 3H), 2.70 (s, 3H); LC-MS: m/z 562.05 [M+H]$^+$; HPLC: 99.54%.

N-(4-chlorophenyl)-N-methyl-2-(4-oxo-2-thioxothiazolidin-3-yl)acetamide (2A): To a stirred solution of 2-(4-oxo-2-thioxothiazolidin-3-yl)acetic acid (1 g, 5.22 mmol) in DCM (50 mL) oxalyl chloride (994 mg, 7.83 mmol) and DMF (0.5 mL) (Cat.) were added at 0° C. The reaction mixture was stirred at rt for 30 min. All volatiles were evaporated and crude material was dissolved in DCM (50 mL). 4-Chloro-N-methylaniline (739 mg, 7.22 mmol) and TEA (1.58 g, 15.66 mmol) was added at 0° C. The reaction mixture was stirred for 1 h at rt. The progress of the reaction was monitored by TLC. After completion of reaction, dilute reaction mixture with DCM and wash with water. Combined organic layer was washed with brine, dried over anhydrous Na$_2$SO$_4$ and concentrated under reduced pressure. The crude compound was purified by column chromatography (50% EA:Hexane) to afford N-(4-chlorophenyl)-N-methyl-2-(4-oxo-2-thioxothiazolidin-3-yl)acetamide (300 mg, 19%) as a yellow solid. ¹H NMR (400 MHz, DMSO-d6): δ 7.60-7.52 (m, 4H), 4.39 (s, 2H), 4.33 (s, 2H), 3.16 (s, 3H); LC-MS: m/z 314.90 [M+H]⁺.

Example #7—NADi-359: (E)-2-(4-(4-((4H-1,2,4-triazol-3-yl)methoxy)-3-fluoro-5-methoxybenzylidene)-3-methyl-5-oxo-2-thioxoimidazolidin-1-yl)-N-(4-chlorophenyl)acetamide

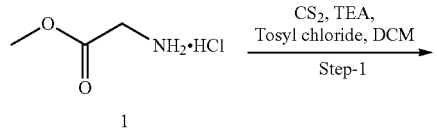

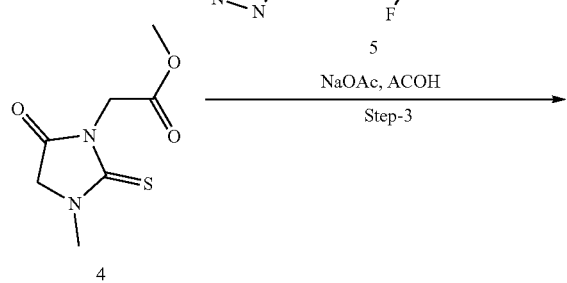

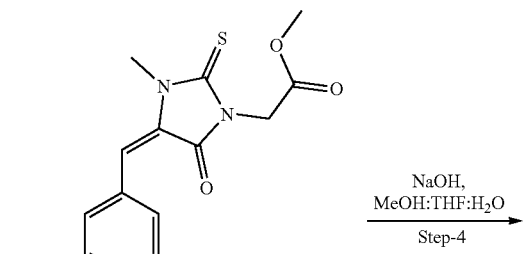

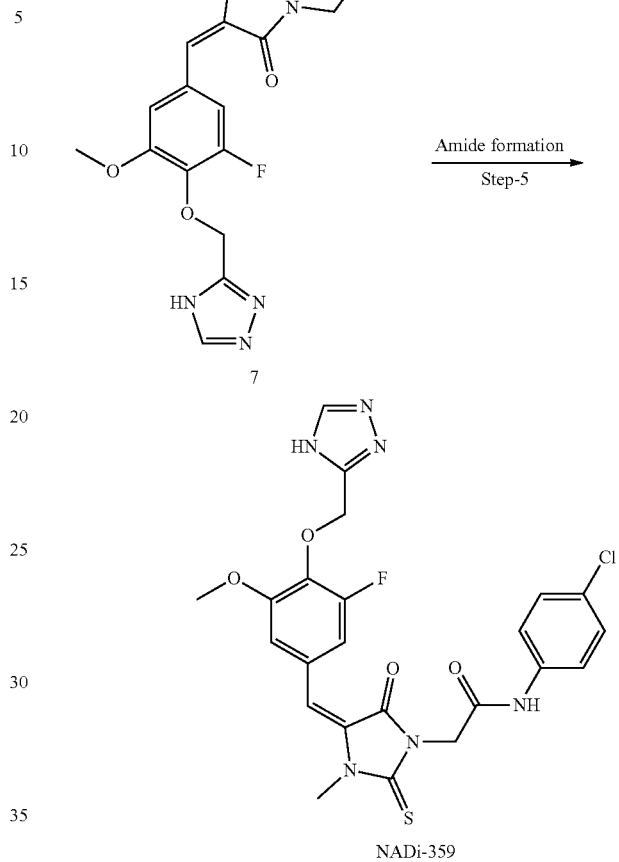

Methyl 2-isothiocyanatoacetate (2): To a stirred solution of methyl glycinate hydrochloride (2 g, 15.92 mmol) in DCM (50 mL), carbon disulfide (1.2 g, 15.92 mmol) and TEA (6.7 mL, 47.76 mmol) was added at 0° C. The reaction mixture was stirred for 30 min and tosyl chloride (3.92 g, 20.6 mmol) was added at rt. The reaction mixture was stirred for 4 h. The progress of the reaction was monitored by TLC. The progress of the reaction was monitored by TLC. After completion of reaction, reaction mixture was diluted with DCM and washed with citric acid solution. Combined organic layer was washed with brine, dried over anhydrous Na₂SO₄ and concentrated under reduced pressure to afford methyl 2-isothiocyanatoacetate (2 g) as an off white solid which was used for next step without purification.

Methyl 2-(3-methyl-5-oxo-2-thioxoimidazolidin-1-yl)acetate (4): To a stirred solution of methyl 2-isothiocyanatoacetate (2 g) in DCM (50 mL), methyl methylglycinate (2.2 g, 15.92 mmol) and TEA (2.24 mL, 15.92 mmol) were added at rt. The reaction mixture was stirred for 2 h. The progress of the reaction was monitored by TLC. After completion of reaction, reaction mixture was diluted with DCM and washed with water. Combined organic layer was washed with brine, dried over anhydrous Na₂SO₄ and concentrated under reduced pressure. The crude compound was purified by column chromatography (5% MeOH:DCM) to afford methyl 2-(3-methyl-5-oxo-2-thioxoimidazolidin-1-yl)acetate (400 mg, 12.38%) as an off white solid. ¹H NMR (400 MHz, DMSO-d6): δ 4.48 (s, 2H), 4.41 (s, 2H), 3.68 (s, 3H), 3.24 (s, 3H).

Methyl (E)-2-(4-(4-((4H-1,2,4-triazol-3-yl)methoxy)-3-fluoro-5-methoxybenzylidene)-3-methyl-5-oxo-2-thioxo-imidazolidin-1-yl)acetate (6): To a stirred solution of 4-((4H-1,2,4-triazol-3-yl)methoxy)-3-fluoro-5-methoxy-benzaldehyde (490 mg, 1.95 mmol) in acetic acid (20 mL), methyl 2-(3-methyl-5-oxo-2-thioxoimidazolidin-1-yl)acetate (411 mg, 2.14 mmol), sodium acetate (809 mg, 9.75 mmol) were added. The reaction mixture was stirred at 90° C. for 16 h. The progress of the reaction was monitored by TLC. After completion of reaction, the reaction mixture cooled and quenched with ice cold water. The solid material was filtered off wash with water and dried well afford 6 as an off white solid (450 mg, 53%). $^1$H NMR (400 MHz, DMSO-d6): δ 13.99 (s, 1H), 8.52 (s, 1H), 7.82-7.75 (m, 2H), 6.98 (s, 1H), 5.13 (s, 2H), 4.67 (s, 2H), 3.86 (s, 3H), 3.70 (s, 3H), 3.60 (s, 3H); LC-MS: m/z 436.10 $[M+H]^+$.

(E)-2-(4-(4-((4H-1,2,4-triazol-3-yl)methoxy)-3-fluoro-5-methoxybenzylidene)-3-methyl-5-oxo-2-thioxoimidazoli-din-1-yl)acetic acid (7): To a stirred solution of methyl (E)-2-(4-(4-((4H-1,2,4-triazol-3-yl)methoxy)-3-fluoro-5-methoxybenzylidene)-3-methyl-5-oxo-2-thioxoimidazoli-din-1-yl)acetate (500 mg, 1.03 mmol) in MeOH:THF:Water (20 mL), NaOH (82 mg, 2.06 mmol) was added. The reaction mixture was stirred at 60° C. for 2 h. The progress of the reaction was monitored by TLC. After completion of reaction, the reaction mixture was cooled and quenched with ice cold water. The solid material was filtered off wash with water. Dried well to afford 7 as an off white solid (450 mg, 93%). LC-MS: m/z 422.10 $[M+H]^+$.

To a stirred solution of (E)-2-(4-(4-((4H-1,2,4-triazol-3-yl)methoxy)-3-fluoro-5-methoxybenzylidene)-3-methyl-5-oxo-2-thioxoimidazolidin-1-yl)acetic acid (400 mg, 0.94 mmol) in DMF (5 mL), HATU (535 mg, 1.41 mmol), 4-chloroaniline (120 mg, 0.94 mmol) and DIPEA (242 mg, 1.82 mmol) were added. The reaction mixture was stirred at rt for 16 h. The progress of the reaction was monitored by TLC. After completion of reaction, reaction mixture was added to ice cold water and extracted aqueous layer with EtOAc. Combined organic layer was washed with brine, dried over anhydrous $Na_2SO_4$ and concentrated under reduced pressure. The crude compound was purified by column chromatography to afford NADi-359 (150 mg, 30%) as a light yellow solid. $^1$H NMR (400 MHz, DMSO-d6): δ 14.00 (brs, 1H), 10.42 (s, 1H), 8.53 (brs, 1H), 7.59-7.57 (m, 2H), 7.40-7.37 (m, 2H), 7.08-7.03 (m, 2H), 6.89 (s, 1H), 5.09 (s, 2H), 4.67 (s, 2H), 3.87 (s, 3H), 3.34 (s, 3H); LC-MS: m/z 531.15 $[M+H]^+$; HPLC: 98.94%.

Notch Complex Assembly Assay

All recombinant proteins were expressed using baculovirus expression vectors in SF21 cells and purified. Unless otherwise stated, all assays contained 125 fmol of double stranded oligonucleotide, CSL, Notch1 and MAML1 proteins. Reactions were carried out in Tris-buffered saline with 0.1% Tween ("TBS-T") buffer containing 0.2% bovine serum albumin ("BSA") and 100 µg/mL salmon sperm DNA. Briefly, the Notch complex was assembled on a biotinylated double stranded ("DS") oligonucleotide harboring one CSL binding site (5'-AAACACGCCGTGG-GAAAAAATTTATG-3'). Complex assembly was quantitated using ALPHASCREEN technology (Perkin Elmer). Proteins in the complexes were detected using specific antibodies to either MAML1 (Cell signaling, D3K7B), Notch1 (Abcam, 52627) or CSL (anti-His, Abcam 18184). Streptavidin conjugated acceptor beads (Perkin Elmer, 6760002) were used to bind the DS oligonucleotide, and Protein-A conjugated donor beads (Perkin Elmer, 6760137) were used to detect antibody-coated proteins. For screening compounds, Notch transcriptional activation complex ("NTC") components were added to wells that already contained the inhibitor to be assayed and allowed to incubate for 30 minutes. The ALPHASCREEN plate (Perkin Elmer, 6008350) was then read on an Envision Plate reader (Perkin Elmer) as specified by the manufacturer.

DNA Affinity Purification

Streptavidin agarose beads (Pierce) were incubated with previously annealed 47-mer biotinylated dsDNA containing two high-affinity CSL binding sites facing forward (2×CSL binding DNA) or 2 mutated CSL binding sites (mut. DNA). Sequences were previously reported by Weaver et al. (2014) Cancer Res. The nuclear lysates of OE33 cell lines were incubated with the DNA streptavidin beads, and bound proteins were analyzed by Western blot. Protein analysis was carried out using conventional SDS-PAGE and transfer techniques. Blots were probed with the indicated antibody ("Ab"), using standard conditions, and detected using enhanced chemiluminescence ("ECL"). The following Ab were used: anti-Notch1$^{val1744}$ (4147S, Cell Signaling Technology), anti-Notch2$^{val1697}$ (SAB4502022, Sigma-Aldrich), anti-Notch3 (5276S, Cell Signaling), anti-CSL (5313S, Cell signaling), anti-SP1 (5931S, Cell Signaling), and anti-GAPDH (ab9483 Abcam).

Cell Lines

OE33 cells, human esophageal adenocarcinoma cell lines, were obtained from the European Collection of Cell Culture. SUM-149 and SUM-159, breast cancer cell lines, were obtained from Dr. Joyce Slingerland at the University of Miami School of Medicine. The following cell lines were obtained directly from the ATCC: 786-0, a human renal cell adenocarcinoma cell line; HT-1080, a human fibrosarcoma cell line; MCF-7, a mammary gland adenocarcinoma; T47D, a human mammary ductal carcinoma cell line; and H-23 a non-small cell lung adenocarcinoma cell line. All cell lines were propagated in growth media as specified.

Colony Assay

Cells were plated into a 6 well plate at a density of 2000 cells/cm$^2$. Inhibitor treatment commenced 24 hours post seeding, and the media containing inhibitor was changed every 48 hours thereafter. After 168 hours, cells were fixed with ice cold methanol for 10 minutes, stained for 1 hour with crystal violet, de-stained with water, and allowed to dry.

Mouse Xenograft Studies

Six-week-old NOD-SCID gamma ("NSG") mice were purchased from Jackson Laboratories and CD-1 Nude mice were purchased from Charles River Laboratories. For the cell line based xenografts assay, 5×10$^6$ OE19 cells in 200 µl serum-free culture medium were injected subcutaneously per mouse. The mice in the treatment group were injected with 15 mg/kg NADi-351 daily, and the mice in the control group were injected with the same volume of vehicle (DMSO). Subcutaneous tumor growth was measured once every 4 days using calipers along with body weight. The experiment was discontinued on day 28. PDX cancer models were established, as described in Zhang et al, Establishment of Patient-Derived Xenograft (PDX) Models of Human Breast Cancer, Current Protocols in Mouse Biology, 3:21-29 (2013), in NSG mice. Briefly, 10 mm$^3$ pieces of primary EAC47 PDX tumor were transplanted subcutaneously into the flanks of NSG mice using a 13G telescopic needle. When the tumors reached 200 mm$^3$, the mice were split into two uniform groups for treatment. NADi-351 (20 mg/kg) and vehicle were administered daily by intraperitoneal ("IP") injection for 24 days. Tumor growth was monitored every 4 days and tumor volume was measured by the formula: Volume=(S×S×L)/2, where S and L are the short and long dimensions. The xenograft tumors were harvested, weighed and samples were subjected to histological examination and by qPCR.

Quantitative RT-PCR Other Assays

RNA was isolated from OE33 cells treated with either DMSO (vehicle) or NADi-351 for 48 h, using an RNA purification kit (Qiagen), following the manufacturer's instructions. cDNA was synthesized using the High Capacity cDNA Reverse Transcription kit (Applied Biosystems), according to the manufacturer's instructions. qPCR reactions were carried out in the Bio-Rad CFX96 thermal cycler using Sybr Green Master Mix (Bio-Rad). Gene expression was normalized to housekeeping gene TBP. Please provide protocols for all outstanding assays used to generate the data in this application.

Pharmacokinetic Studies

Pharmacokinetic studies were performed as previously described (Astudillo et al. (2016) Cancer Res). The following treatments were administered: NADi-260 via intraperitoneal (i.p.) route at 100 mg/kg, NADI-260 via intravenous route (i.v.) at 2 mg/kg, NADi-351 via i.p. at 10 mg/kg, NADi-351 via i.p at 10 mg/kg and NADi-351 via oral route (PO) at 50 mg/kg. Blood samples were collected from each treatment group and their respective control grounds, plasma was separated from blood immediately by centrifugation at 4000 rpm for 10 min at 4° C. and stored below –70° C. until bioanalysis. All samples were processed for analysis by protein precipitation using acetonitrile and analyzed by fit for purpose LC-MS/MS method. Pharmacokinetic parameters were calculated using the non-compartmental analysis module of Phoenix WinNonlin (Version 6.3).

Histological Analysis of Mouse Intestine Tissue

Six-week old BALB/c mice (Jackson Laboratories) were injected intraperitoneally with NADi-351, daily for 5 days. Small intestine samples were harvested on day 5. Formalin-fixed and paraffin-embedded tissues were sectioned at 3 μm thickness. Histochemical identification of intestinal cell types was performed with Periodic Acid-Schiff (PAS) staining kit (ab150680, Abcam), according to manufacturer's instructions.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:

1. A compound of Formula (I), or a pharmaceutically acceptable salt thereof:

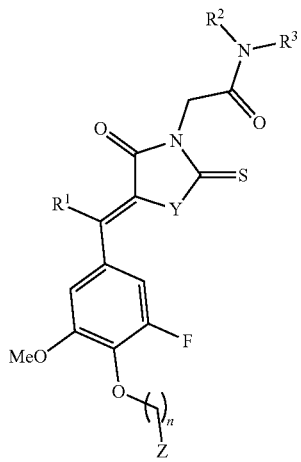

(I)

wherein:
n is 1 or 2;
Y is O, S or $NC_{1-3}$alkyl;
Z is triazolyl;
$R^1$ is H or $C_{1-3}$alkyl;
$R^2$ is H or $C_{1-3}$alkyl; and
$R^3$ is $C_{1-3}$alkyl or halophenyl.

2. The compound or salt of claim 1, wherein n is 1.

3. The compound or salt of claim 1, wherein n is 2.

4. The compound or salt of claim 1, wherein Y is O or $NCH_3$.

5. The compound or salt of claim 1, wherein Y is S.

6. The compound or salt of claim 1, wherein Z is

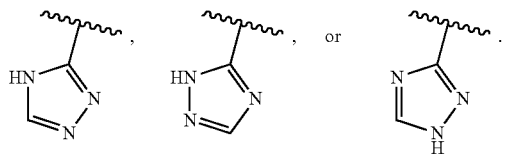 [SMILES: *c1nnc[nH]1 ; *c1ncn[nH]1 ; *c1nc[nH]n1]

7. The compound or salt of claim 6, wherein Z is

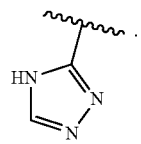

8. The compound or salt of claim 1, wherein $R^1$ is H or $CH_3$.

9. The compound or salt of claim 1, wherein R² is H or CH₃.

10. The compound or salt of claim 1, wherein R³ is CH₃.

11. The compound or salt of claim 1, wherein R³ is chlorophenyl.

12. The compound or salt of claim 1, wherein:

(i) R² is CH₃ and R³ is CH₃;

(ii) R² is H and R³ is chlorophenyl; or (iii) R² is CH₃ and R³ is chlorophenyl.

13. The compound or salt of claim 11, wherein R³ is para-chlorophenyl.

14. The compound or salt of claim 1, wherein n is 1; Y is S; R¹ is CH₃; R² is CH₃; and R³ is CH₃.

15. The compound or salt of claim 1, wherein the compound is selected from the group consisting of:

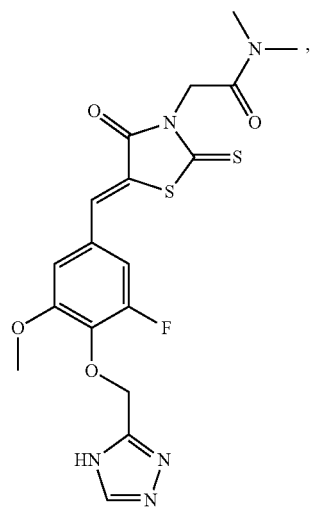

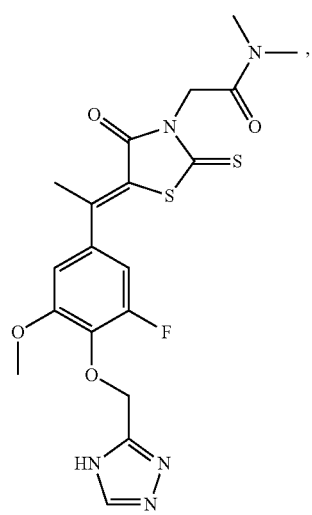

-continued

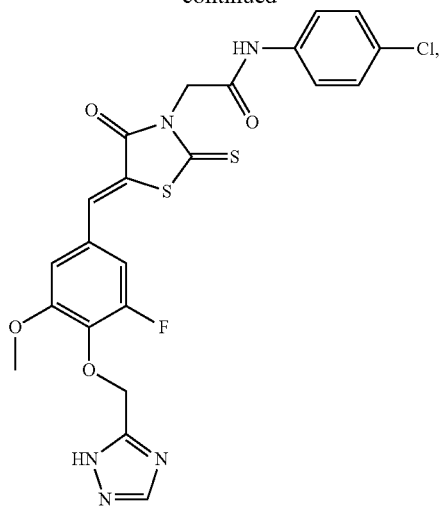

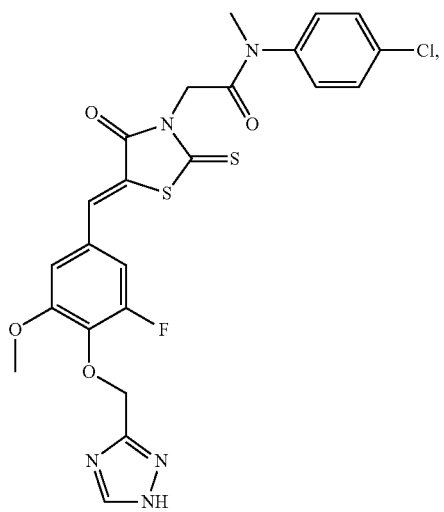

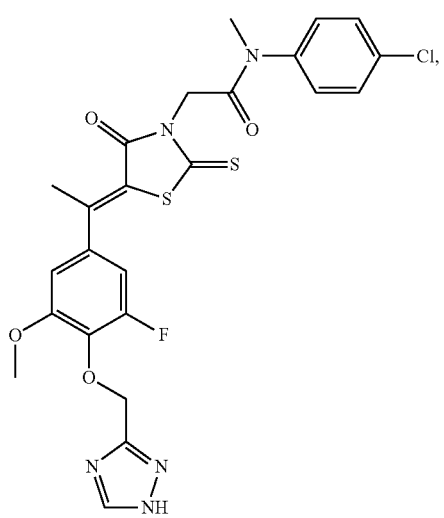

-continued

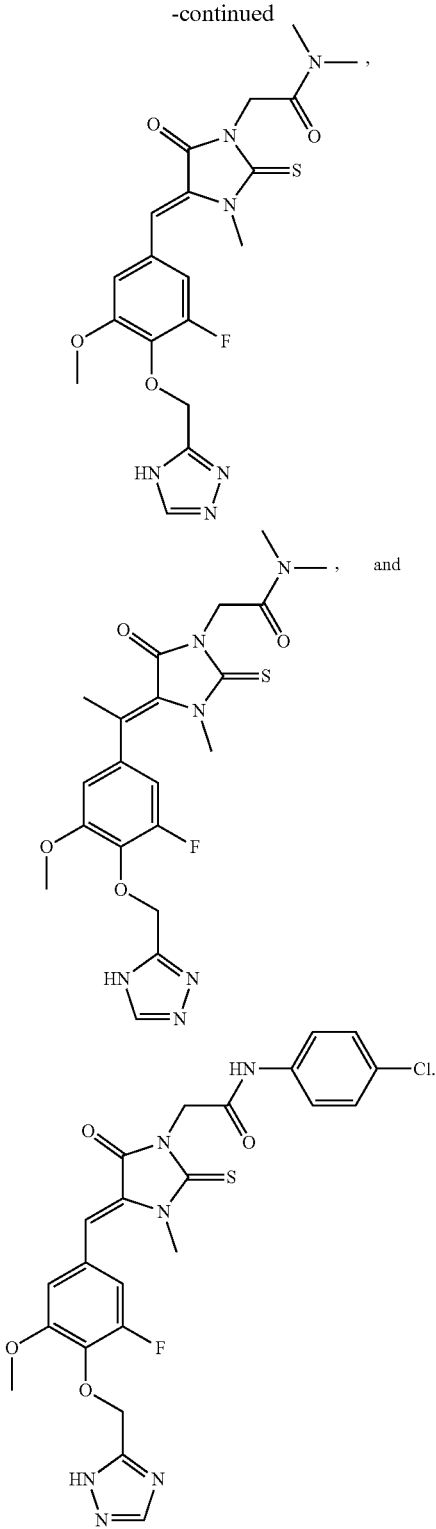

16. The compound or salt of claim 15 having a structure:

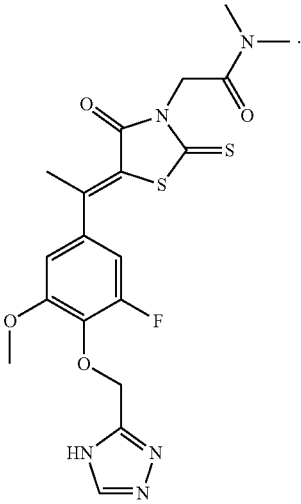 [SMILES: COc1cc(/C(C)=C2\SC(=S)N(CC(=O)N(C)C)C2=O)cc(F)c1OCc1nnc[nH]1]

17. A pharmaceutical composition comprising the compound or salt of claim 1 and a pharmaceutically acceptable excipient.

18. A method of inhibiting the Notch transcriptional activation complex ("NTC") in a cell, comprising contacting the cell with the compound or salt of claim 1, in an amount effective to inhibit the NTC.

19. A method of treating Tetralogy of Fallot ("TOF"), Alagille syndrome, cerebral autosomal-dominant ateriopathy with sub-cortical infarcts and leukoencephalophathy ("CADASIL"), or multiple sclerosis ("MS"), comprising administering to a patient in need thereof a therapeutically effective amount of the compound of claim 1.

20. A method of treating cancer selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, chronic lymphocytic leukemia ("CLL"), hepatocellular carcinoma ("HCC"), myelomonocytic leukemia ("CMML"), pancreatic ductal adenocarcinoma ("PDAC"), head and neck squamous cell carcinoma ("HNSCC"), renal cell adenocarcinoma, gastric and esophageal cancers, and fibrosarcoma comprising administering to a patient in need thereof a therapeutically effective amount of the compound of claim 1.

* * * * *